(12) United States Patent
Heavner

(10) Patent No.: US 8,323,585 B2
(45) Date of Patent: Dec. 4, 2012

(54) USE OF FLUID ASPIRATION/DISPENSING TIP AS A MICROCENTRIFUGE TUBE

(75) Inventor: David A. Heavner, Fairport, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 0 days.

(21) Appl. No.: 13/542,272

(22) Filed: Jul. 5, 2012

(65) Prior Publication Data

US 2012/0276654 A1 Nov. 1, 2012

Related U.S. Application Data

(62) Division of application No. 12/174,336, filed on Jul. 16, 2008, now abandoned.

(51) Int. Cl.
*B01L 3/00* (2006.01)
(52) U.S. Cl. ........ 422/500; 422/501; 422/524; 422/533; 436/180; 222/251
(58) Field of Classification Search .......... 422/500–501, 422/524, 533; 436/180; 222/251
See application file for complete search history.

(56) References Cited

U.S. PATENT DOCUMENTS

| | | |
|---|---|---|
| 3,929,943 A | 12/1975 | Klimaszewski, Jr. |
| 3,992,158 A | 11/1976 | Przybylowicz et al. |
| 4,101,422 A | 7/1978 | Lamont et al. |
| 4,147,628 A | 4/1979 | Bennett et al. |
| 4,190,535 A | 2/1980 | Luderer et al. |
| 4,305,721 A | 12/1981 | Bernstein |
| 4,496,293 A | 1/1985 | Nakamura et al. |
| 4,743,561 A | 5/1988 | Shaffar |
| 4,798,577 A | 1/1989 | Brenneman et al. |
| 4,818,418 A | 4/1989 | Saunders |
| 4,933,291 A | 6/1990 | Daiss et al. |
| 4,956,298 A | 9/1990 | Diekmann |
| 5,256,376 A | 10/1993 | Callan et al. |
| 5,384,239 A | 1/1995 | Saunders |
| 5,552,064 A | 9/1996 | Chachowski et al. |
| 5,650,068 A | 7/1997 | Chachowski et al. |
| 5,665,558 A | 9/1997 | Frame et al. |
| 5,722,553 A | 3/1998 | Hovatter |
| 5,753,186 A | 5/1998 | Hanley et al. |
| 5,846,492 A | 12/1998 | Jacobs et al. |
| 6,001,310 A | 12/1999 | Shaffer et al. |
| 6,013,528 A | 1/2000 | Jacobs et al. |
| 6,096,561 A | 8/2000 | Tayi |

(Continued)

FOREIGN PATENT DOCUMENTS

EP 743095 11/1996

(Continued)

OTHER PUBLICATIONS

European Search Report for EP Application No. 09251798.6; mailed Oct. 15, 2009; 5 pages.

*Primary Examiner* — Jyoti Nagpaul
(74) *Attorney, Agent, or Firm* — Hiscock & Barclay, LLP

(57) ABSTRACT

A fluid aspirating/dispensing member includes a sample cavity for sample acquisition and a sealable cavity that, once sealed, permits the separation of particles from the remainder of a fluid sample within the sample cavity after centrifugation or other separation means. The fluid aspirating/dispensing members, either individually or as part of an array, increase the efficiency of sample processing before analysis by a clinical analyzer.

14 Claims, 13 Drawing Sheets

U.S. PATENT DOCUMENTS

| | | |
|---|---|---|
| 6,326,155 B1 | 12/2001 | Maclennan et al. |
| 6,334,842 B1 | 1/2002 | Hlavinka et al. |
| D453,573 S | 2/2002 | Lafond et al. |
| 6,596,546 B1 | 7/2003 | Jolley et al. |
| 6,601,725 B2 | 8/2003 | Lafond et al. |
| 6,622,882 B2 | 9/2003 | Smith |
| 6,761,855 B1 | 7/2004 | Cook et al. |
| 6,797,518 B1 | 9/2004 | Jacobs et al. |
| 6,979,534 B1 | 12/2005 | Siegel |
| 7,064,823 B2 | 6/2006 | Roche et al. |
| 7,217,561 B2 | 5/2007 | Wirix-Speetjens |
| 7,250,303 B2 | 7/2007 | Jakubowicz et al. |
| 7,282,372 B2 | 10/2007 | VanBrunt et al. |
| 2001/0019842 A1 | 9/2001 | Kitamura et al. |
| 2003/0022380 A1 | 1/2003 | Jakubowicz et al. |
| 2003/0026733 A1 | 2/2003 | LaCourt et al. |
| 2004/0072367 A1 | 4/2004 | Ding et al. |
| 2004/0166551 A1 | 8/2004 | Moulds et al. |
| 2005/0123444 A1 | 6/2005 | Tomasso et al. |
| 2005/0181519 A1 | 8/2005 | Karg et al. |
| 2005/0208676 A1 | 9/2005 | Kahatt |
| 2005/0504832 | 9/2005 | Jessop |
| 2007/0003443 A1 | 1/2007 | Sandell et al. |
| 2007/0017927 A1 | 1/2007 | D'Amore et al. |

FOREIGN PATENT DOCUMENTS

| | | |
|---|---|---|
| EP | 1542020 | 6/2005 |
| GB | 1 512 685 | 6/1978 |
| JP | A-62-273065 | 11/1987 |
| JP | 07-083936 | 3/1995 |
| WO | WO 92/20778 | 11/1992 |
| WO | WO 98/16312 | 4/1998 |
| WO | WO 99/06149 | 2/1999 |
| WO | WO 99/47261 | 9/1999 |
| WO | WO 2006/016528 A1 | 2/2006 |

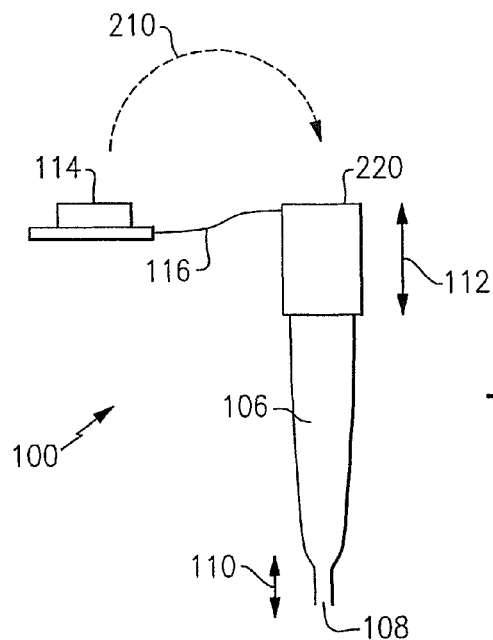
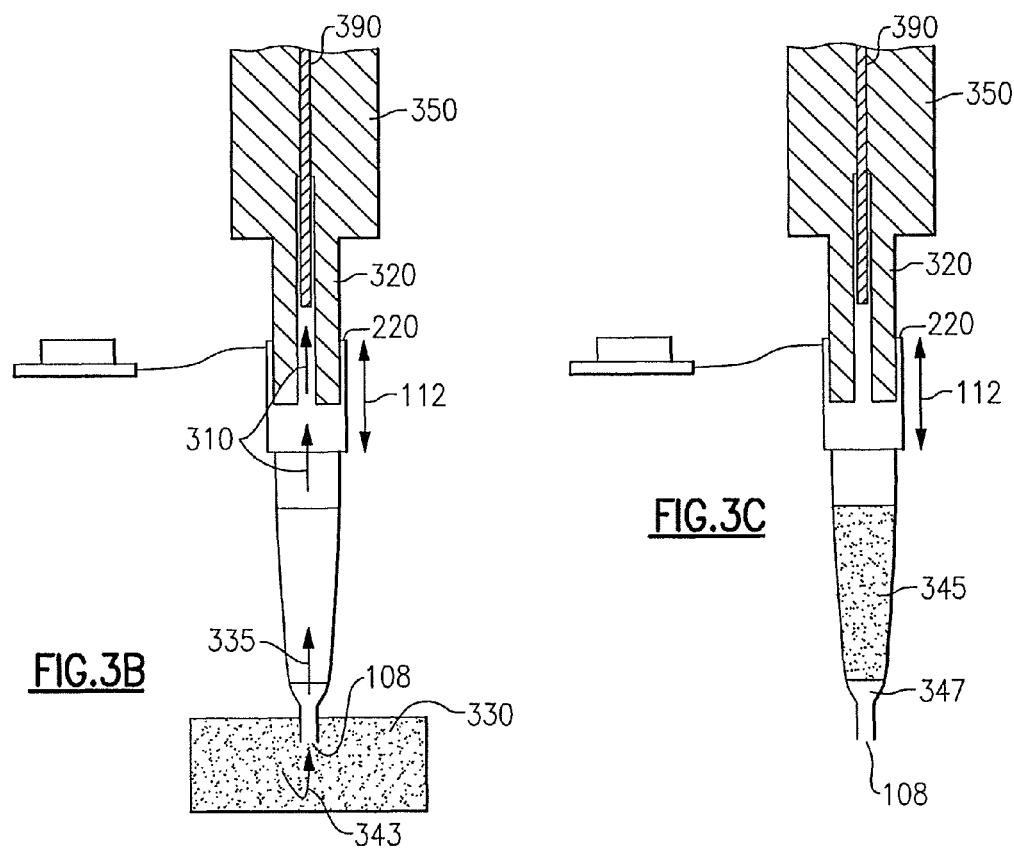

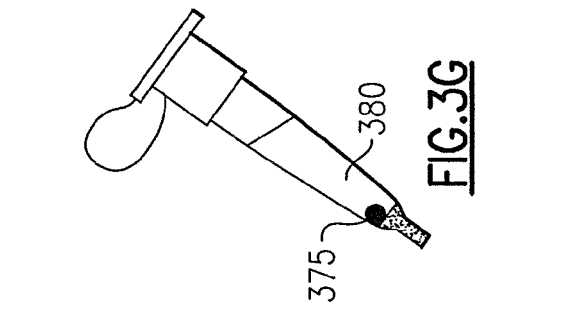
FIG.3G
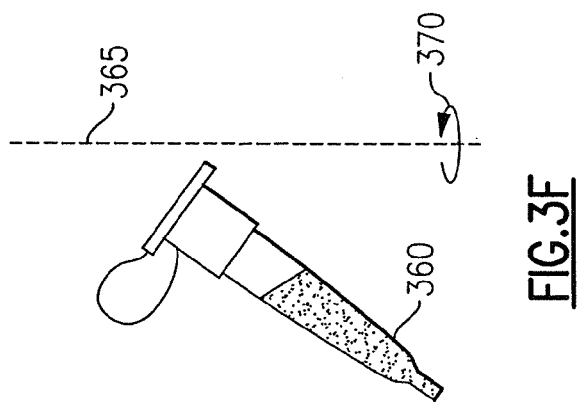
FIG.3F
FIG.3E
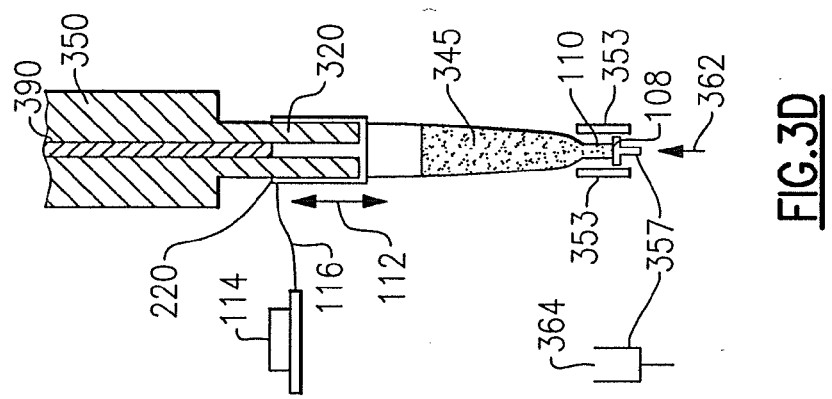
FIG.3D

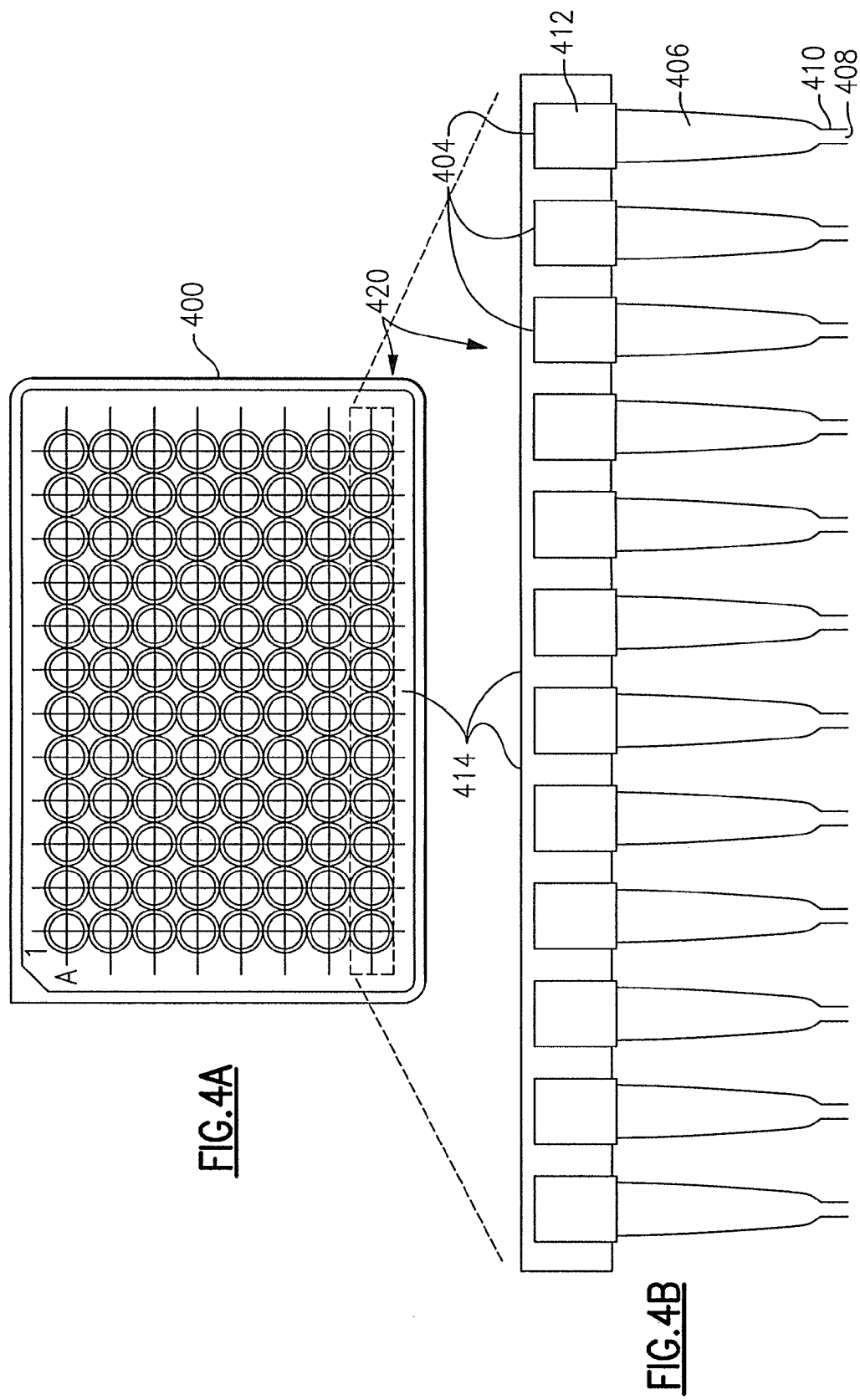

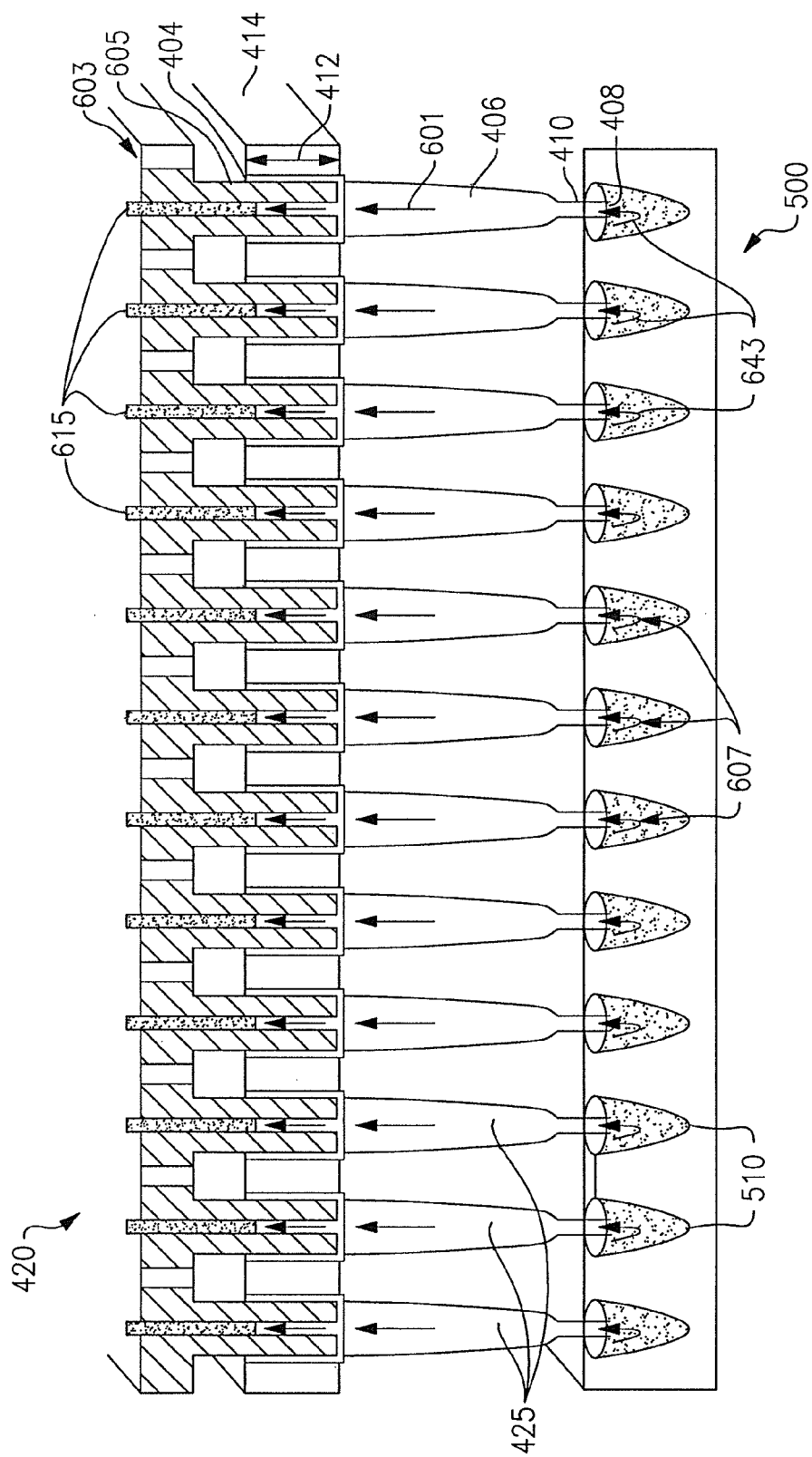

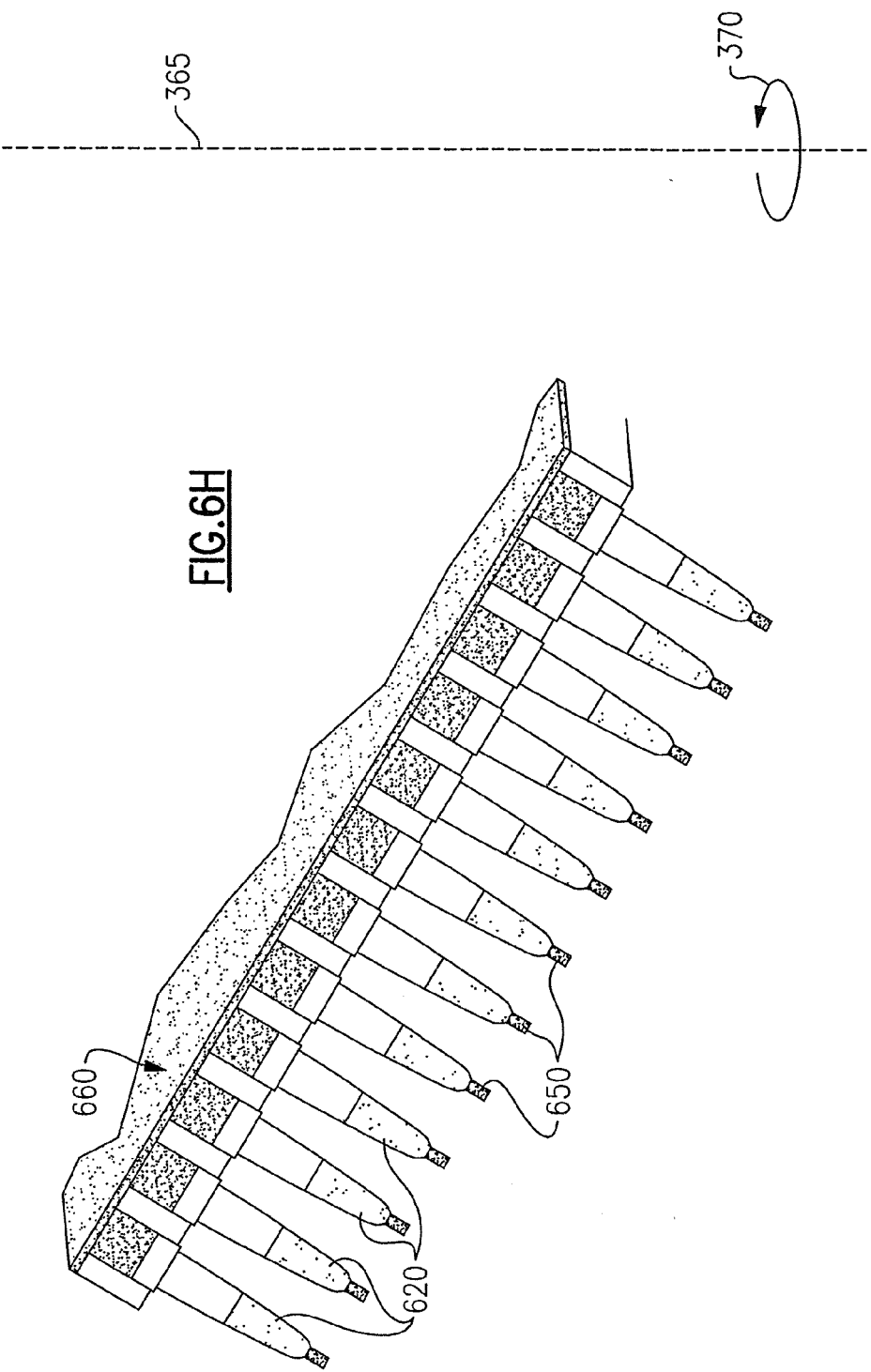

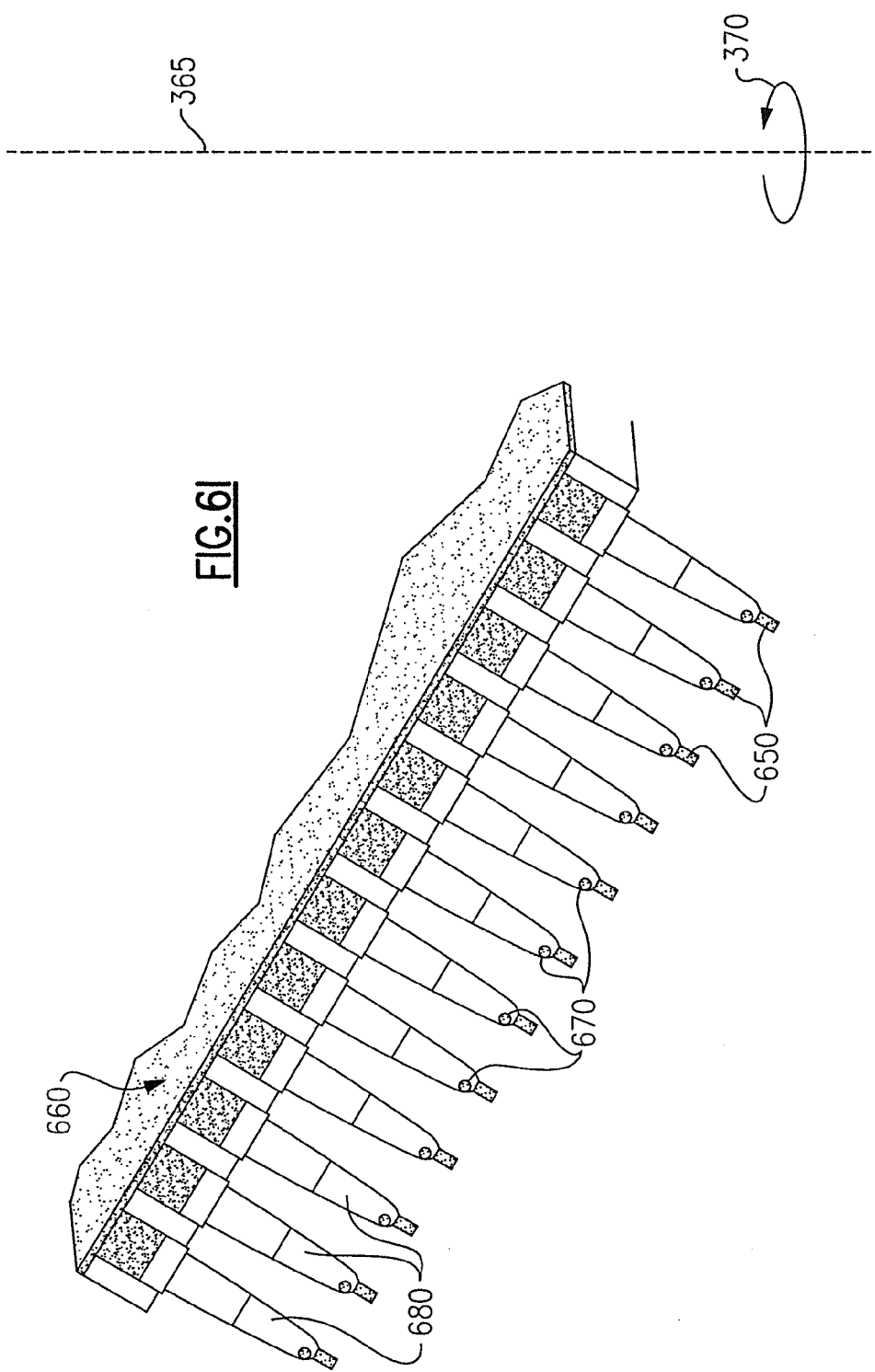

USE OF FLUID ASPIRATION/DISPENSING TIP AS A MICROCENTRIFUGE TUBE

CROSS REFERENCE TO RELATED APPLICATION

This application is a divisional application of U.S. Ser. No. 12/174,336, filed on Jul. 16, 2008, the entire contents of which are incorporated by reference.

FIELD OF THE APPLICATION

This application relates to an apparatus and a method for sample collection and centrifugation within a single, disposable fluid aspirating/dispensing member.

BACKGROUND OF THE INVENTION

Combinational clinical analyzers containing both "wet" and "dry" chemistry platforms in a single apparatus for the testing of biological samples, such as whole blood serum, are now widely used in most modern health care facilities.

So-called "dry" chemistry systems commonly include a sample supply, a number of sample containers, a metering/transport mechanism, and an incubator having a plurality of test read stations as described, for example, in U.S. Pat. No. 3,992,158, the contents of which are hereby incorporated herein by reference in its entirety. A typical protocol starts with the aspiration of a known quantity of a sample into a fluid aspirating/dispensing member. An aliquot of the sample is then dispensed onto a dry slide element which is then loaded into an incubator. After appropriate incubation, the amount or presence of at least one analyte in the sample is determined using, for example, an electrometer, reflectometer or other suitable testing devices.

So-called "wet" chemistry systems on the other hand, use a reaction vessel, such as a cuvette, which receives predetermined volumetric quantities of sample, reagent, and other fluids that are appropriately metered into a reaction vessel in order to perform an assay(s). The "wet" chemistry system commonly includes a metering mechanism to transport a patient sample fluid from a sample supply to the reaction vessel. After a pre-determined incubation period during which one or more reactions occur, a measuring device, such as an optical measuring device is used to pass a beam of light through the reaction vessel and sample. Assays typically used in 'wet' chemistry systems include, but are not limited to, spectrophotometric absorbance assays such as end point reaction analysis and rate of reaction analysis, turbidimetric assays, nephelometric assays, radiative energy attenuation assays (such as those described in U.S. Pat. Nos. 4,496,293 and 4,743,561, the contents of which are hereby incorporated herein by reference in their entirety), ion capture assays, color, metric assays, and fluorometric assays, and immunoassays, all of which are well known in the art.

Integration of wet/dry chemistry capabilities into clinical analyzers reduces experimental error, improves work flow and limits the need for human intervention thereby reducing the risk of contamination of lab personnel with human pathogens. One example of a commercially available combination clinical analyzer employing both wet and dry chemistry systems is the Vitros 5,1 FS Chemistry System, which is described in further detail in U.S. Pat. No. 7,250,303 and U.S. Patent Publication No. US 2003/0026733 (each assigned to OrthoClinical Diagnostics, Rochester, N.Y.), the contents of which are incorporated herein by reference in its entirety.

Despite the progress that has been made, these systems still require that patient samples be first processed to remove particulate components before presentation to a clinical analyzer. This processing step remains cumbersome, time consuming and limits the overall efficiency of these analyzers.

Information relevant to attempts to address this problem can be found in U.S. Pat. Nos. D453,573; 4,933,291; 5,384,239; 5,722,553; 5,753,186; 6,001,310; 6,334,842; 6,601,725; 6,622,882; 7,064,823; the published U.S. Publication Numbers US 2001/0019842; US 2005/0204832; US 2005/0208676; US 2007/0003443, US 2007/0017927; International PCT application PCT/AU1992/000236 and European Patent No. EP743095. Each one of these references suffers, however, from one or more of the following disadvantages: the references fail to remedy the inefficient processing of patient samples prior to clinical analysis and also fail to describe a fluid aspirating/dispensing member that permits both sample collection and centrifugation.

For the foregoing reasons, there is an unmet need in the field to improve the efficiency of sample processing prior to analysis by clinical analyzers.

SUMMARY OF THE APPLICATION

The invention pertains to a fluid aspirating/dispensing member having a sealable end that can be used for both sample collection and centrifugation. Methods are described for performing sample collection and centrifugation using either individual fluid members or plates comprising a plurality of fluid aspirating/dispensing members.

According to one version, a fluid aspirating/dispensing member is described that comprises a first port, a second port, opposite the first port, and a cap. The cap is configured to releasably close the first port when attached thereto. The internal volume of the fluid aspirating/dispensing member comprises a sample cavity between the first and second ports; and a sealable cavity between the second port and the sample cavity. The sealing of the sealable cavity seals the second port to create a container that is configured to retain a fluid sample in the sample cavity and to permit the separation of particles suspended in the sample from the remainder of the sample.

According to another aspect, the fluid aspirating/dispensing member is configured to be placed within a testing apparatus capable of separating particles from the remainder of the fluid sample. The apparatus may be a clinical analyzer. The separation of the particles from the remainder of the sample can result, for example, from centrifugation.

In one aspect, the walls of the sample cavity are tapered, whereas the walls of the sealable cavity can be parallel with respect to the vertical axis of the fluid aspirating/dispensing member.

The sealable cavity of the fluid aspirating/dispensing member can be heat-sealable, less than 1 cm long, with walls that are less than 2 mm apart and parallel to the vertical axis of the aspirating/dispensing member.

In one aspect, the cap is removably attached to the aspirating/dispensing member.

The aspirating/dispensing member can allow for optical or visual testing of a sample, which can be a cell suspension or blood. Particles within the sample can be red blood cells.

The aspirating/dispensing member can further contain a separation barrier or reagents for agglutination within the internal volume of each member.

According to another version, a fluid aspirating/dispensing plate is described that comprises an array of fluid aspirating/dispensing members attached to a solid support. Each of the aspirating/dispensing members comprises a first port and a second port, opposite the first port. The internal volume of each fluid aspirating/dispensing member comprises a sample cavity between the first and second ports; and a sealable cavity between the second port and the sample cavity. The sealing of the sealable cavity of each of the fluid aspirating/dispensing members creates a plurality of containers that are configured to retain a fluid sample in the sample cavity and permit the separation of particles suspended in the sample from the remainder of the sample.

In one aspect, the solid support is planar that can include a means for supporting the fluid aspirating/dispensing members. The fluid aspirating/dispensing plate can have 96 fluid aspirating/dispensing members.

In another aspect, the fluid aspirating/dispensing members are reversibly attached to the solid support.

In another version, the fluid aspirating/dispensing plate is configured to be placed within a testing apparatus capable of separating particles from the remainder of the sample of each the fluid aspirating/dispensing member. This testing apparatus can be a clinical analyzer.

The separation of the particles from the remainder of the sample can result from separation by centrifugation.

The sealable cavity of the fluid aspirating/dispensing plate can be a heat-sealable cavity.

In another version, the fluid aspirating/dispensing plate has a cover that is configured to close each of the first ports when the cover is placed on the first ports of the fluid aspirating/dispensing plate.

In one aspect, the fluid aspirating/dispensing members of the plate allow for optical or visual testing of a sample within the internal volume of each member.

In another aspect, the array of aspirating/dispensing members on the plate align with the wells of a microtiter plate. Each well of the microtiter plate can retain a sample that is different from each of the other wells in the plate, wherein the sample can be a cell suspension or blood. Particles within the sample can be cells.

In yet another aspect, the aspirating/dispensing members on the plate can contain a separation barrier or reagents for agglutination within the internal volume of each member.

According to another embodiment, a method is described for separating particles in a fluid sample, the method comprising the steps of (a) loading a fluid aspirating/dispensing member into an apparatus, the member comprising a first port, a second port and a sample cavity in fluid communication with the first and second ports, (b) aspirating a sample into the sample cavity through the second port of the fluid aspirating/dispensing member, (c) sealing the second port of the fluid aspirating/dispensing member to create a fluid container; (d) closing the first port using a cap sized to releasably engage and cover the first port; and (e) separating particles in the sample from the remainder of the sample, wherein the separated particles and sample are retained within the sample cavity of the fluid aspirating/dispensing member for detection of the particles or sample.

The apparatus can be a clinical analyzer. The separating step can be performed, for example, by centrifugation.

According to one aspect, the loading step requires the attachment of the fluid aspirating/dispensing member to a proboscis of a metering mechanism of the apparatus.

In another aspect, the fluid aspirating/dispensing member is a metering tip.

In one aspect, the sealing step is performed by heat sealing the second port of the fluid aspirating/dispensing member.

According to yet another embodiment, a method is described for separating particles in a plurality of fluid samples, the method comprising the steps of (a) loading a fluid aspirating/dispensing plate into an apparatus, wherein the plate comprises a plurality of fluid aspirating/dispensing members, each of the members comprising a first port, a second port and a sample cavity in fluid communication with each of the first and second ports, (b) aspirating a plurality of samples into the sample cavities through the second ports of each of the fluid aspirating/dispensing members, (c) sealing the second ports of each of the fluid aspirating/dispensing members to create a plurality of fluid containers and (d) separating particles in the sample from the remainder of the sample in each of the containers, wherein the particles and sample are retained within the sample cavity of each of the fluid aspirating/dispensing members for detection of the particles or sample.

In one aspect, the apparatus is a clinical analyzer.

The separating step can be performed by centrifugation.

In one aspect the loading step requires the attachment of the fluid aspirating/dispensing plate to a plurality of proboscis of a metering mechanism of the apparatus.

In another aspect, the fluid aspirating/dispensing members are metering tips.

According to another embodiment, after the aspirating step, the first ports of each of the fluid aspirating/dispensing members are closed by a lid that is configured to close the first ports of each of the fluid aspirating/dispensing members when it is placed on the first ports of the fluid aspirating/dispensing members.

The sealing step can be performed by heat sealing the second ports of each of the fluid aspirating/dispensing members.

The previously described embodiments have many advantages, including the ability to perform sample collection and particle separation using either individual disposable fluid aspirating/dispensing members or a fluid aspirating/dispensing plate comprising a plurality of fluid aspirating/dispensing members. The methods described herein reduce handling errors as well as the time spent for sample processing before analysis by clinical analyzers. Sample processing using the herein described fluid aspirating/dispensing member is therefore faster than conventional methods known in the art.

It should be understood that this application is not limited to the embodiments disclosed in this Summary, and it is intended to cover modifications and variations that are within the scope of those of sufficient skill in the field, and as defined by the claims.

BRIEF DESCRIPTION OF THE DRAWINGS

FIGS. 3A-3G depict sequential cross-section views of the fluid aspirating/dispensing member of FIG. 1 representing a method of sample collection and centrifugation in accordance with a second embodiment;

FIG. 4A depicts a view of a fluid aspirating/dispensing plate comprising an array of fluid aspirating/dispensing members in accordance with a third embodiment;

FIG. 4B depicts a cross-sectional view of a row of fluid aspirating/dispensing members of the plate of FIG. 4A;

FIGS. 6A-6I depict sequential cross-section views of the array of fluid aspirating/dispensing members of FIG. 4A representing a method of sample collection and centrifugation in accordance with a fourth embodiment.

DETAILED DESCRIPTION

Figure 1:
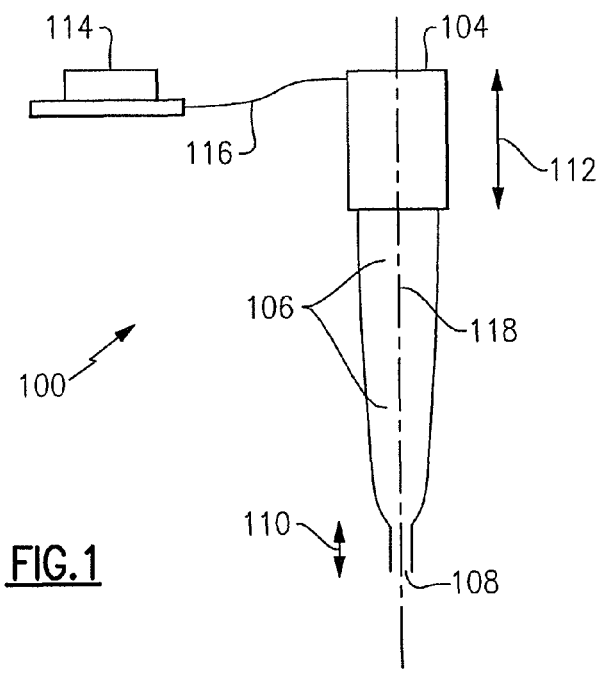
FIG. 1 depicts a cross-sectional view of a fluid aspirating/dispensing member made in accordance with one embodiment.

Unless defined otherwise, all technical and scientific terms used herein have the same meaning as is commonly understood by one of skill in the art. The following definitions are provided to help interpret the disclosure and claims of this application. In the event a definition in this section is not consistent with definitions elsewhere, the definition set forth in this section will control.

As used herein, "combinational" analyzer refers to a clinical analyzer that includes at least two chemistry systems that can encompass any combination of "dry" and/or "wet" chemistry systems.

As used herein, a "clinical analyzer" refers to any apparatus capable of analyzing clinical samples including, but not limited to, immunodiagnostic analyzers as well as analyzers for the automated "wet" and/or "dry" chemistry analysis of clinical samples. "Wet" chemistry platforms typically include a microprocessor controlling an automated fluid handling system that aspirates and dispenses one or more samples and/or reagents into a reaction vessel, at least one sample reservoir, optionally at least one reagent reservoir, at least one incubator and at least one detector, such as a spectrophotometer. Typical analyzers for use with the fluid aspirating/dispensing member of this application are described in further detail in U.S. Pat. Nos. 6,096,561, 7,282,372 and 7,250,303, all of which are incorporated herein by reference in their entireties. In a preferred embodiment, the clinical analyzer used herein refers to commercially available analyzers such as the VITROS 5,1 FS Chemistry System manufactured by Ortho-Clinical Diagnostics, Inc.

An element is in "fluid communication" with another element when a fluid is able to travel from one element to the other such as via capillary action and/or gravity. The elements may be in direct contact, but do not need to be in direct contact; i.e., other elements through which said fluid can pass may be intervening. An element is "not in fluid communication" with another element when a fluid is not able to travel from one element to the other via capillary action and/or gravity. Typically, the elements are physically separated, i.e. spaced apart.

As used herein, a "fluid aspirating/dispensing member" is a device such as a metering tip containing one or more internal cavities in fluid communication with two or more sealable apertures that is used for both sample collection and particle separation as described in U.S. Pat. No. 6,797,518, the contents of which are hereby incorporated by reference herein in its entirety. In one embodiment, the particle separation occurs as a result of centrifugation. A fluid aspirating/dispensing member typically performs the aspiration or dispensing of a volumetric amount of a sample within a clinical analyzer. In one embodiment, the fluid aspirating/dispensing member is composed of a molded, solid material that can be centrifuged without deformation of the internal cavities. In another embodiment, the material does not promote the adhesion of a biological sample to the internal walls of the fluid aspirating/dispensing member. In another embodiment the fluid aspirating/dispensing member is made out of a plastic material typically by extrusion blow molding. The fluid aspirating/dispensing member can be made from a thermoplastic material preferably having a translucent or transparent characteristic that allows optical testing to be performed upon the fluid contents after aspiration therein. In one embodiment, the fluid aspirating/dispensing member is made of a moldable plastic such as polypropylene or polyethylene. In another embodiment, the fluid aspirating/dispensing member is made of a homopolymer or copolymer such as a polyallomer, wherein one of the monomers is propylene. In yet another embodiment, the fluid aspirating/dispensing member is made of polyethylene terephthalate.

As used herein, a "fluid aspirating/dispensing plate" refers to an array of multiple fluid aspirating/dispensing members attached to a solid support. Each fluid aspirating/dispensing member comprises one or more internal cavities in fluid communication with two or more sealable apertures for both sample collection and particle separation. A fluid aspirating/dispensing plate is typically used for the aspiration or dispensing of a volumetric amount of one or more samples within a clinical analyzer. In one embodiment, the support is planar and rectangular or square in shape, although the fluid aspirating/dispensing plate described herein may have any shape. In another embodiment, the fluid aspirating/dispensing members on the fluid aspirating/dispensing plate are arranged in rows, each row having the same number of fluid aspirating/dispensing members. In another embodiment, the fluid aspirating/dispensing plate comprises a support for the fluid aspirating/dispensing members. A person of skill in the art will recognize that the support can be engineered to facilitate centrifugation and robotic handling in a clinical analyzer. In one embodiment, the fluid aspirating/dispensing members are reversibly affixed to the solid support. In another embodiment, the multiple fluid aspirating/dispensing members are arrayed on a fluid aspirating/dispensing plate in such a manner so as to align with the wells of a microtiter plate. In yet another embodiment, the plate has a plurality of locations for the reversible attachment of one, two, five, ten, 25, 50, 75, 100 or more fluid aspirating/dispensing members. Each location on the plate may or may not be filled with a fluid aspirating/dispensing member.

As used herein, "separation of the particles from the remainder of the sample" refers to any procedure that permits the separation of the liquid phase of a sample from its solid particulate phase. In one embodiment, the "separation of the particles from the remainder of the sample" refers to the partial or complete separation of the solid particulate phase of a sample from its liquid phase within the sample cavity of the fluid aspirating/dispensing member after the sealing of the fluid aspirating/dispensing member. In another embodiment, the separation occurs as a consequence of centrifugation. In yet another embodiment, the separation results from a magnetic field acting on magnetic particles that have been added to a sample.

As used herein, the term "sealable, cavity" refers to a region of the fluid aspirating/dispensing member, located between the sample cavity and the bottom end of the aspirating/dispensing member, which can be sealed, for example, by heat sealing or as a result of the application of a sealant as defined herein. As a consequence of sealing, the sample cavity is no longer in fluid communication with the aspirating/dispensing end of the fluid aspirating/dispensing member thus creating a fluid container for particle separation. In one embodiment, the sealable cavity is made of a thermoplastic melt-fusible material. In another embodiment the thermoplastic melt-fusible material is a polyallomer or similar thermoplastic material suitable for heat sealing as known by a person of skill in the art.

As used herein, "heat sealing" refers to the application of sufficient heat and pressure to the walls of the sealable cavity of the fluid aspirating/dispensing member to cause the walls to fuse together. Subsequent curing i.e. the hardening and solidification of the fused thermoplastic walls creates a pressure-resistant sealing of the sealable cavity that prohibits fluid communication between the sample cavity and the sealable aspirating/dispensing end of the fluid aspirating/dispensing member. A more detailed description of heat sealing can be found in U.S. Pat. No. 3,929,943, the contents of which is hereby incorporated herein in its entirety. In another embodiment, heat sealing is applied to the sealable cavities of a plurality of fluid aspirating/dispensing members arrayed on a fluid aspirating/dispensing plate. For example, the aspirating/dispensing ends of the array of fluid aspirating/dispensing members can be aligned and inserted into an array of metallic molding cups that are heated to a temperature that promotes the melting and fusion of the walls of the sealable cavities placed therein.

As used herein, "sealing" refers to the permanent closing of the aspirating/dispensing end of a fluid aspirating/dispensing member. In one embodiment, sealing refers to heat sealing. In another embodiment, sealing refers to the application of a sealant, for example, a plastic or adhesive, that hermetically plugs the aspirating/dispensing end of a fluid aspirating/dispensing member. In another example, the sealant may be a bottom cap, such as a bottom screw cap, that hermetically closes the aspirating/dispensing end of a fluid aspirating/dispensing member.

As used herein, a "sealant" shall mean any composition such as an adhesive that can be used to form a connecting bond between the walls of the sealable cavity of the fluid aspirating/dispensing member described herein. In one embodiment the sealant is UV curable. In another embodiment, the sealant cures at room temperature.

As used herein, the term "polyallomer" refers to any thermoplastic material that produces copolymers of the 1-olefins exhibiting a degree of crystallinity normally associated only with homopolymers. In one embodiment, the polyallomer is a random block copolymer of propylene and ethylene. In another embodiment, the polyallomer is a readily fusible plastic material sold by Eastman Chemical Co. under the trade name "Tenite® Polyallomer."

As used herein, the term "cavity" refers to any three-dimensional enclosure within the described fluid aspirating/dispensing member. In an exemplary embodiment, one or more cavities are in fluid communication with each other.

The term "plurality," as used herein, refers to a quantity of two or more.

As used herein, "particles" may be cells, for example, bacteria or red blood cells or white blood cells found in a sample. In another embodiment, particles may be microscopic solids that are added to a sample prior to sample processing. These particles may be inert solids in the form of beads, beaded gels or microspheres, although they may have any shape. Further examples of particles include, but are not limited to, plastic particles, ceramic particles, carbon particles, polystyrene microbeads, latex beads, glass beads, magnetic beads, hollow glass spheres, metal particles, particles of complex compositions, microfabricated or micromachined particles. Inert particles may be comprised of any suitable material, such as glass or ceramics, organic materials such as carbon or plastic and/or one or more polymers, such as, for example, nylon, polytetrafluoroethylene (TEFLON™) or styrene-divinylbenzene polymers. The particle size may be from about 0.1 micron to 1000 microns. Preferably, the particle size is from about 1 to about 10 microns. In principle, any ligand may be covalently bound to a solid-phase matrix or particle such as agarose beads (e.g., Sepharose Pharmacia) using known techniques, for example as described by Hearn et al., Methods in Enzymology Vol. 35:102-117 (1987). Generally, the beads are first activated by a chemical agent, such as glutaraldehyde, carbonyldiimidizole, cyanogen bromide hydroxysuccinimide, tosyl chloride or the like. The chosen ligand is then covalently attached to the beads, resulting in an extremely stable linkage of the ligand to the support.

As used herein, "cell suspension" refers to a mixture of cells in a liquid typically found in a sample. Cells can be eukaryotic or prokaryotic cells. In one embodiment, the cells are bacteria. In another embodiment, the cells are pathogenic bacteria. In a preferred embodiment, the cells are blood cells. In another preferred embodiment, the cells are red blood cells.

As used herein, the term "sample" refers to a material suspected of containing at least one analyte. The sample can be used directly as obtained from the source or following a pretreatment to modify the character of the sample. The sample can be derived from any biological source, such as a physiological fluid, including, blood, plasma, saliva, ocular lens fluid, cerebral spinal fluid, sweat, urine, milk, ascites fluid, raucous, synovial fluid, peritoneal fluid, amniotic fluid or the like. The sample can be pretreated before use. For example, whole blood is typically treated with a polyanion such as heparin and the like to inhibit blood coagulation. In another example, viscous fluids can be diluted. Methods of treatment can also include filtration, distillation, concentration, inactivation of interfering components, and the addition of reagents. Besides physiological fluids, other liquid samples can be used. In addition, a solid material suspected of containing an analyte can be used as the sample. In some instances it may be beneficial to modify a solid sample to form a liquid medium or to release the analyte. In another embodiment, a sample, as defined herein, is understood to include one or more compounds that may be added to the sample before or during analysis, including, but not limited to, buffers, reagents, peptides, enzymes, ligands, ligand-binding molecules, antibodies, particles, ligand-bound particles, magnetic particles, and the like. A sample, as defined herein, may contain particles as defined above.

The term "analyte," as used herein, refers to any compound or composition or entity to be detected or measured. An analyte can be any inorganic or organic molecule or cellular component or cell or organism that is tested for by clinical assays known in the art. Clinical assays may test for either the presence or absence of an analyte. In one embodiment, an analyte has at least one epitope or binding site or ligand. In another embodiment, an analyte can be any substance for which there exists a naturally occurring binding member or for which a binding member can be prepared. In yet another embodiment, an analyte refers to a population of cells, for example, blood cells such as white blood cells, red blood cells (hematocrit) or platelets. Analytes may also include, but are not limited to, metabolites, toxins, inorganic or organic compounds, proteins, peptides, cytokines, chemokines, enzymes, amino acids, lipids, HDL/LDL cholesterol, triglycerides, polysaccharides, blood glucose, nucleic acids, hormones (for example, thyroid stimulating hormone (TSH), Adrenocorticotropic hormone (ACTH), prolactin), steroids (for example, cortisol or testosterone or estrogen), vitamins, electrolytes, drugs, ions (for example, for pH measurements), trace metals, microorganisms (bacteria, viruses or parasites and the like), virus particles, metabolites of and antibodies to any of the above substances. In another embodiment, the analyte is C reactive protein, albumin, amylase, D-dimer, bilirubin, alkaline phosphatase, gamma glutamyl transferase, urea, creatine, serum iron, transferring, prostate specific antigen (PSA), alpha fetoprotein (AFP), beta Human chorionic gonadotrophin (bHCG), alpha 1-antitrypsin (AAT), CA-125 (also CA12.5), carcinoembryonic antigen (CEA), fibrinogen or any other compound which is typically tested for in a clinical sample. The term "analyte" may include any antigenic substances, haptens, antibodies, macromolecules and combinations thereof. In another embodiment, the analyte is an enzyme that can be detected by measuring enzyme activity. For example, the testing for creatine kinase, glutamic oxaloacetic transaminase (SGOT), serum glutamic pyruvic transaminase (SGPT) activity in blood is widely used as an indicator of liver or heart damage.

As used herein, a "ligand" is any molecule which is capable of binding to a ligand-binding molecule. In one embodiment, the ligand is an epitope of an antibody. A number of ligands are also known that bind immunoglobulin molecules and may be covalently coupled to the particles used in this application, for example Protein A, Protein G, Protein A/G and KappaLock™ (see also U.S. Pat. No. 5,665,558, the contents of which are herein incorporated by reference in its entirety). The ligand may bind to the isotype of the antibody which is used or tested for or, alternatively, one may use a bridging antibody, e.g., an IgG antiIgM, for an IgM antibody. Thus, an IgG anti-IgM antibody would be coupled to the ligand as a "bridge" and an IgM antibody would bind to the IgG anti-IgM antibody.

The term "ligand-binding," as used herein, refers to a member of a binding pair, i.e., two different molecules wherein one of the molecules specifically binds to the second molecule through chemical or physical means. In addition to antigen and antibody binding pair members, other binding pairs include, as examples without limitation, biotin and avidin, carbohydrates and lectins, complementary nucleotide sequences, complementary peptide sequences, polysaccharides and lectins, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, binding pairs can include members that are analogs of the original binding member, for example, an analyte-analog or a binding member made by recombinant techniques or molecular engineering. If the binding member is an immunoreactant it can be, for example, a monoclonal or polyclonal antibody, a recombinant protein or recombinant antibody, a chimeric antibody, a mixture(s) or fragment(s) of the foregoing, as well as a preparation of such antibodies, peptides and nucleotides for which suitability for use as binding members is well known to those skilled in the art. A ligand-binding member may be a polypeptide affinity ligand (see, for example, U.S. Pat. No. 6,326,155, the contents of which are hereby incorporated by reference herein in its entirety). In one embodiment, the ligand-binding member is labeled. The label may be selected from a fluorescent label, a chemiluminescent label or a bioluminescent label, an enzyme-antibody construct or other similar suitable labels known in the art.

As used herein "blood" broadly includes whole blood or any component of whole blood, such as red blood cells, white blood cells, plasma or serum.

As used herein, "centrifugation" refers to the rotation of an object about an axis of rotation. Samples may be centrifuged in a fixed angle or swing bucket rotor or any other rotor known in the art.

As used herein, "STAT" is a medical term derived from the Latin word "statim" which means immediately. A "STAT lane" therefore refers to the urgent or rush processing of patient samples.

As used herein, "emergency sample" refers to any sample that requires immediate processing. Emergency samples typically include those samples collected in emergency rooms or other urgent care facilities. For example, an emergency room sample can be a blood sample taken from a patient in an emergency room.

"Agglutination," as used herein refers to the clumping of a suspension of cellular or particulate antigen by a reagent, usually an antibody or other ligand-binding entities (see, for example, U.S. Pat. Nos. 4,305,721, 5,650,068 and 5,552,064, the contents of which are hereby incorporated herein by reference in their entirety). In one embodiment, the reagent is Coomb's reagent.

As used herein, "Coomb's reagent" refers to a preparation of antibodies, raised in animals, directed against one of the following human immunoglobulin, complement or a specific immunoglobulin e.g. anti-human IgG for use in the Coomb's test.

As used herein, "detection" refers to the detection of light absorption or light scattering using a photodetector (see, for example, U.S. Pat. No. 5,256,376 and published U.S. patent application US 2004/0166551, the contents of which are hereby incorporated herein by reference in their entirety). In one embodiment, detection refers to the detection of bioluminescence or chemiluminescence or fluorescence (see, for example, U.S. Pat. No. 6,596,546, the contents of which are hereby incorporated herein by reference in its entirety).

As used herein, the term "agitating" refers to a force acting on the contents of a fluid aspirating/dispensing member, for example a centrifugal force or a force induced by a magnetic field.

As used herein, a "metering device," as used herein, refers to a component of a clinical analyzer that can reversibly attach to a fluid aspirating/dispensing member by means of a proboscis. In one embodiment, metering devices, controlled by an on-board computer, coordinate the movement and/or transport of fluid aspirating/dispensing members or a fluid aspirating/dispensing plate within a clinical analyzer.

As used herein, the term "proboscis" refers to a component of a clinical analyzer that attaches to one or more aspirating/dispensing members, either individually or as part of a fluid aspirating/dispensing plate. In one embodiment, the proboscis is part of a metering mechanism and can be cylindrical in shape and fits within the proboscis receptacle region of each of one or more fluid aspirating/dispensing members in such a manner as to insert itself against the internal wall of the proboscis receptacle region of a fluid aspirating/dispensing member in an air-tight manner (i.e., there is no substantial leak of air between the cylindrical surface of the proboscis and the wall). Once the proboscis is hermetically affixed to the proboscis receptacle region of each of the fluid aspirating/dispensing member, the proboscis by means of the metering mechanism, confers either a vacuum or pressure to the internal volume of each fluid aspirating/dispensing member and thereby drives the movement of a known volume of fluid within the internal cavities of each fluid aspirating/dispensing member.

As used herein, the term "separation barrier" refers to a water immiscible, typically thixotropic, gel-like or bead=like material having a density intermediate between that found for the light, liquid phase and the heavy, substantially particulate phases of a sample. For example, the separation barrier is typically disposed in the sample cavity of the fluid aspirating/dispensing member which is then filled with the sample. Upon centrifugation, the sample is gradient separated into its two phases and the barrier material migrates to the interface between the phases. Upon completion of centrifugation, the separation barrier forms a physical and chemical barrier between the separated phases, thereby preventing any mixing of the phases. Separation barriers can be, for example, a mixture of silicone fluids and fine hydrophobic silica powder, a polyester material or a hydrocarbon gel-like material such as a polybutane or any other material known in the art. The composition of separation barrier materials is described in further detail in U.S. Pat. Nos. 4,190,535; 4,101,422; 4,818,418 and 4,147,628, the contents of which are hereby incorporated herein in their entirety.

As used herein, the term "antibody" includes both polyclonal and monoclonal antibodies; and may be an intact molecule, a fragment thereof (such as Fv, Fd, Fab, Fab' and F(ab)'2 fragments, or multimers or aggregates of intact molecules and/or fragments; and may occur in nature or be produced, e.g., by immunization, synthesis or genetic engineering. The antibody or antigen used herein is dependent upon the antibody or antigen that is being tested. For example, the number of blood group antigens and thus, antibodies to these antigens that have been identified is very large, with more antigens and antibodies continually being determined. The International Society of Blood Transfusion has published a non-exclusive list of red cell antigens in Blood Group Terminology 1990, Vox. Sang. 58:152-169 (1990 and includes, but is not limited to, antibodies and antigens A, B, D, C, c, Cw, E, e, K, Fya, Fyb, Jka, Jkb, S and s.

With the preceding definitions as noted herein, the following description relates to certain preferred embodiments of the application, and to a particular methodology for the initial processing of patient samples prior to chemical analysis. As will be readily apparent from the discussion, the inventive concepts described herein can also be suitably applied to other methods that require the efficient processing of patient samples. In addition, such terms as "top," "bottom," "lateral," "above," "below" and the like are also used in order to provide a convenient frame of reference for use with the accompanying drawings. These terms, unless stated specifically otherwise, however, are not intended to be limiting of the present invention. A novel fluid aspirating/dispensing member is described herein that permits both sample collection and particle separation by centrifugation or other separation means, thereby increasing the efficiency of sample processing before analysis by the wet/dry chemistry components of a combinational clinical analyzer.

According to a first embodiment, FIG. 1 shows a sealable fluid aspirating/dispensing member 100 for sample collection and particle separation. The fluid aspirating/dispensing member 100 is typically composed of an injection-moldable, preferably transparent, thermoplastic material such as polypropylene, polyallomer, polyethylene terephthalate, co-polymers or blends of polymers or any other suitable inert material known in the art. Preferably, the sample being analyzed does not adhere to the walls of the internal volume of the fluid aspirating/dispensing member 100 wherein these surfaces of the fluid aspirating/dispensing member 100 may be treated to avoid such adherence of the sample or reagents to the internal surfaces of the fluid aspirating/dispensing member 100. The internal volume of a fluid aspirating/dispensing member 100 may be from about 1 microliter to about 2000 microliters or more. In one example, the internal volume is from about 1 microliter to about 500 microliters. In a preferred embodiment, the fluid aspirating/dispensing member 100 has an internal volume of about 1 microliter to about 300 microliters. The thickness of the wall of a fluid aspirating/dispensing member 100 is not critical provided it can withstand centrifugation without deformation. Typically, the wall has a thickness from about 5 mm to about 0.1 mm, from about 2 mm to about 0.5 mm or from about 1.5 mm to about 0.75 mm. As shown in FIG. 1, the fluid aspirating/dispensing member 100 is defined at an upper end by an input port 104 and at a lower end by a sealable input port 108. Between input ports 104 and 108 is an internal cavity comprising a sample cavity 106 which is in fluid communication with input ports 104 and 108. The input port 104 is configured to attach hermetically to the proboscis of a metering mechanism (not shown in this view) for the movement of known volumes of air from the internal volume of the fluid aspirating/dispensing member 100. In one embodiment, the proboscis 320 inserts hermetically through the input port 104 into a proboscis receptacle region 112 of the fluid aspirating/dispensing member 100. The sealable input port 108 is configured to permit aspiration or dispensing of fluids through the input port 108 and into the sample cavity 106. The walls of the sealable cavity can be thinner than those of the sample cavity 106 to facilitate heat sealing. In one version, the internal volume of the fluid aspirating/dispensing member 100 may be preloaded with reagents that are required for clinical analysis, for example, reagents for blood agglutination or blood typing. In another embodiment, the sample cavity of the fluid aspirating/dispensing member 100 contains a separation barrier as defined herein.

Figure 2:
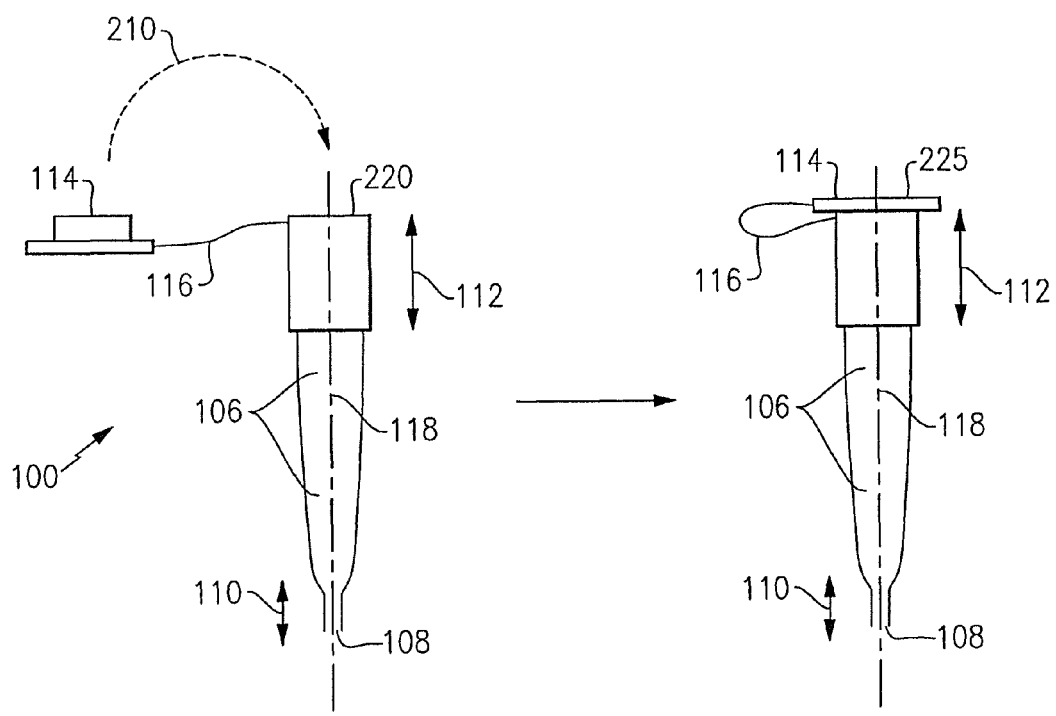
FIG. 2 illustrates the movement of the cap of the fluid aspirating/dispensing member of FIG. 1.

Referring now to FIGS. 1 and 2, the herein described fluid aspirating/dispensing member 100 is shown with an optional cap 114 connected to the upper end of the member 100 by means of a tether 116. The tether 116 may be of any length as long as it does not interfere with sample collection or particle separation, i.e., centrifugation. For example, the tether 116 may be from about 0.5 cm to about 2 cm in length or from about 0.5 cm to about 1 cm in length. By bending the tether 116 in the direction 210, the cap 114 can be reversibly inserted into the input port 104. In one version, the cap 114 is not attached to the fluid aspirating/dispensing member 100 (not shown) and is therefore inserted directly into input port 104 before centrifugation. The placement of the cap 114 over input port 104 forms a hermetic seal that prevents fluids in the sample cavity 106 from escaping through input port 104 during centrifugation and/or handling of the fluid aspirating/dispensing member 100. In another version, the fluid aspirating/dispensing member 100 does not require a cap. In yet another embodiment, the input port 108 may be sealed using a sealant as defined herein that is cured after being inserted into the sealable cavity 110.

Referring to FIGS. 1, 2 and 3A, the herein described fluid aspirating/dispensing member 100 includes a heat sealable cavity 110 that is disposed between the sample cavity 106 and the sealable input port 108. Application of heat to the heat sealable cavity 110 causes the thermoplastic material of the walls to melt and fuse thus sealing the sealable input port 108. Other methods may also be employed to seal input port 108. For example, a sealant, such as an adhesive, may be applied to the input port 108 and cured by cooling or other means, for example, localized exposure to UV radiation. In another version, the input port 108 is hermetically closed using a bottom cap, for example, a bottom screw cap (not shown).

With the foregoing structural description of a fluid aspirating/dispensing member 100, a method is now described with respect to sample collection and particle separation within a fluid aspirating/dispensing member 100 in accordance with a second embodiment.

Referring to FIG. 3B, the fluid aspirating/dispensing member 100 is shown as attached to a metering mechanism 350 and more specifically a proboscis 320 of a clinical analyzer. The proboscis forms a component of a metering mechanism of the analyzer. Appropriate robotic commands direct the metering system to align the proboscis 320 with the input port 220 of the fluid aspirating/dispensing member 100. After proper alignment, the metering system hermetically inserts the proboscis 320 through the open input port 220 into the proboscis receptacle region 112 of the fluid aspirating/dispensing member 100. The input port 108 is then immersed into the sample 330. The proboscis 320 of the metering mechanism 350 creates a controlled amount of negative pressure within the internal volume of the fluid aspirating/dispensing member 100. The subsequent displacement of air 310 through input port 104 promotes the movement 343 of a defined volume of sample 330 into the sample cavity 106 of the fluid aspirating/dispensing member 100. The volume of the aspirated sample depends on the available volume within the sample cavity 106. In one example, an aliquot of between about 1 to about 1000 microliters of sample 330 is aspirated. In another example, an aliquot of between about 1 to about 300 microliters of sample 330 is aspirated. In yet another example, from about 1 to about 50 microliters of sample 330 is aspirated into the sample cavity 106 of the fluid aspirating/dispensing member 100.

Referring to FIG. 3C, after the aspiration of a sample 330 into the sample cavity 106 is complete, the input port 108 of the fluid aspirating/dispensing member 100 is removed from the sample 330. The proboscis 320 of the metering mechanism 350 again creates a controlled amount of negative pressure within the internal volume of the fluid aspirating/dispensing member 100 that causes a small bubble of air 347 to be aspirated through input port 108 and displaces the aspirated sample 345 away from the input port 108 and into the sample cavity 106 proper. By maintaining the air tight seal between the proboscis 320 and the proboscis receptacle region 112 of the fluid aspirating/dispensing member 100, the sample is retained within the sample cavity 106 prior to heat sealing of the input port 108. This procedure ensures both a reliable seal and limits any temperature rise of the aspirated sample 345 before analysis.

Referring to FIG. 3D, the input port 104 of the fluid aspirating/dispensing member 100 is placed in a heat sealing device 353 while the proboscis 320 remains hermetically inserted in the proboscis receptacle region 112 of the fluid aspirating/dispensing member 100. The thermoplastic material in the walls of the sealable cavity 110 is then rapidly heated to its melting temperature. The speed with which the polymer must be heated to its melt temperature depends on the inherent viscosity of the polymer, the wall thickness and diameter of the sealable cavity 110, as described in detail in U.S. Pat. No. 3,929,943, incorporated herein above. The maximum period for heating can be from about 1 to about 30 seconds or from 5 to about 20 seconds or about 10 to about 15 seconds. The heat sealing device can be a high-intensity radiant heater, such as tungsten or quartz lamp. Alternatively, microwave heaters, such as dielectric heaters or ultrasonic heaters or any other means known in the art can be utilized. The melting temperature can be from about 200 degrees to about 350 degrees Celsius, depending on the thermoplastic properties of the fluid aspirating/dispensing member 100. After the walls of the heat sealable cavity 110 are heated, they are pressed in the direction 362 by a press 357 to force the walls together and seal the open end. In one version, the end of the press 357 is shaped in the form of a cup 364 that fits over the input port 108 of the fluid aspirating/dispensing member 100 and facilitates the fusion and molding of the input port 108 into a sealed end 355. In one version, a metallic press 357 is heated to the appropriate melting temperature and applied directly to the sealable input port 108. After sealing, the input port 108 is rapidly cooled to promote the solidification of the fused thermoplastic material thus producing a hermetically sealed fluid container or cuvette. The press 357 and metering device 320 are then removed.

Referring to FIGS. 3E-3G, a cap 367 can be inserted over input port 104. The fluid aspirating/dispensing member 360 is then robotically placed into a fixed angle or swinging bucket rotor of a centrifuge of a clinical analyzer and rotated in the direction 370 around a vertical axis 365. The port 355 is hermetically sealed and rendered pressure resistant by the heat sealing treatment described above, thereby ensuring the aspirated sample 345 remains within the sample cavity 106 during centrifugation about the vertical axis 365. As a consequence of the centrifugal force acting on the particulate phase of the aspirated sample 345, particles within the sample accumulate in a pellet 375 at the bottom of the sample cavity 106 of the fluid aspirating/dispensing member 100. After centrifugation, the closed cap 367 is removed and the sample supernatant 380 is collected for presentation to either the "wet" and/or "dry" chemistry components of a clinical analyzer.

The sealed fluid aspirating/dispensing member 100, may also be made from a transparent plastic material that permits optical testing of the fluid contents within the fluid aspirating/dispensing member 100. Details relating to the optical reading of the fluid contents of a sample are described in further detail in U.S. Pat. Nos. 6,013,528 and 5,846,492, the entire contents of each are hereby incorporated by reference. In one example, the walls of the fluid aspirating/dispensing member can transmit electromagnetic radiation of a wavelength required for the excitation of a fluorescent ligand and electromagnetic radiation of a wavelength characteristic of the subsequent emission of fluorescence.

According to another version, the fluid aspirating/dispensing member 100 may be preloaded with a separation barrier material, as defined herein, that facilitates the separation of the particulate phase from the liquid phase of a sample during particle separation, for example, centrifugation.

A person of ordinary skill in the art will recognize that the described embodiments can be altered in a number of ways and still fall within the intended scope of the application. For example, the fluid aspirating/dispensing member 100 described herein can be used as part of a series where a second fluid aspirating/dispensing member 100 is used to collect the supernatant 380 of centrifuged sample that was processed in a first aspirating/dispensing member 100. For example, a sample, such as heparinized blood from a patient, can be aspirated into the sample cavity 106 of a first fluid aspirating/dispensing member 100. After the sealing of the sealable cavity 106, the aliquot is centrifuged to pellet the blood cells at the bottom of the sample cavity 106. A second fluid aspirating/dispensing member 100 can then be used to aspirate the serum supernatant 380 into the sample cavity 106 of the second fluid aspirating/dispensing member 100. Sealing of the sealable cavity 110 of the second fluid aspirating/dispensing member 100 creates a reaction vessel that can be robotically transported to the wet/dry components of the clinical analyzer for additional processing. In one version, the fluid aspirating/dispensing member 100 may be attached to a metering mechanism 350 having a proboscis 320 that permits pre-loading of the sample cavity with one or more reagents for clinical analysis, for example, reagents for agglutination, i.e., anti-human immunoglobulin (Coomb's reagent) or other reagents for blood typing. Mixing of the sample with the reagent can be achieved by repeated aspiration and dispensing into a suitable container followed by the aspiration of the homogenized mixture into the sample cavity 106 of the fluid aspirating/dispensing member 100 for further processing.

It will be readily apparent to one of sufficient skill and as described in greater detail that the following description is exemplary and therefore, there is potential to use the fluid aspirating/dispensing member 100 for the processing of, for example, immunoassays comprising ligand-binding molecules attached to various particles such as latex or agarose beads and the like. A number of ligands are known that bind immunoglobulin molecules and may be covalently coupled to the particles, for example Protein A, Protein G, Protein A/G, Kappalock. In one embodiment, the particles may be bound to, for example, bacteriophage expressing a ligand binding entity (see for example, U.S. Pat. No. 6,979,534, the contents of which are hereby incorporated by reference herein in their entirety).

According to one version, assays used in conjunction with the fluid aspirating/dispensing member 100 may include magnetic particles such as magnetic beads. Magnetic particles can be aspirated together with a sample into the sample cavity 106. After the sealing of the sealable cavity 110, the particles are separated from the rest of the sample as described above by simply deploying a powerful magnet adjacent to the sample cavity in the absence of centrifugation. Many methods are known in the art where cells can be rendered magnetic for purposes of cell separation and the like. For example, cells can be incubated with biotinylated antibodies or other ligand-binding molecules that are specific for a surface antigen, characteristic of a particular cell type. Addition of streptavidin-conjugated magnetic beads (Invitrogen/Dynal Biotech) then bind to the biotinylated antibodies and thereby render the cells magnetic and hence amenable to cell separation using a magnetic field. The description of controlled transport of magnetic beads is disclosed in U.S. Pat. No. 7,217,561, the contents of which is hereby incorporated herein in its entirety. Cells used in the invention may also be tagged using labeled antibodies known in the art. For example, the labeled antibodies may be fluorophore-conjugated antibodies. Agglutination can be monitored by the detection of fluorescence emitted from agglutinated cells.

Figure 5:
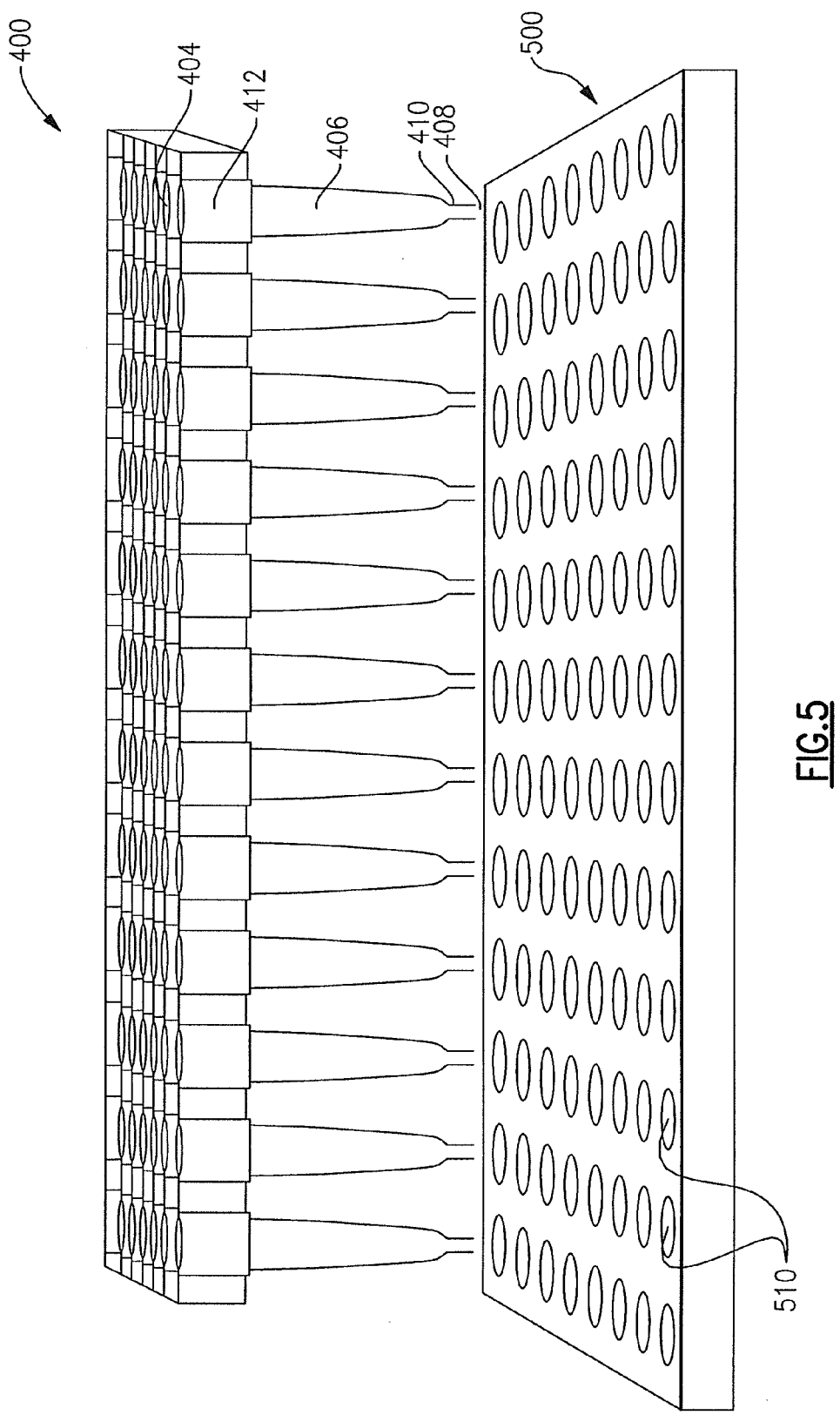
FIG. 5 illustrates the alignment of the array of fluid aspirating/dispensing members of FIG. 4A with a microtiter plate.

In accordance with a third embodiment, FIGS. 4A and 4B illustrate a fluid aspirating/dispensing member assembly configuration that is more amenable to automation and high throughput analysis of a plurality of samples. FIG. 4A depicts a fluid aspirating/dispensing plate 400 on which 96 of the fluid aspirating/dispensing members 100 of FIG. 1 are arranged into 8 rows of 12 fluid aspirating/dispensing members 425. FIG. 4B portrays a cross sectional view of the plate 400 to show row 420 of 12 fluid aspirating/dispensing members 425 attached to a solid support 414. In one version, the attachment may be reversible. Each of the aspirating/dispensing members 425 comprises an input port 404, proboscis receptacle region 412 attached to a solid support 414, a sample cavity 406, a sealable cavity 410 and sealable input port 408. FIG. 5 illustrates how the sealable input ports 408 of the fluid aspirating/dispensing plate 400 can align with the wells 510 of a microtiter plate 500.

With the foregoing structural description of a fluid aspirating/dispensing plate 400 of fluid aspirating/dispensing members, a method is now described with respect to sample collection and particle separation using a fluid aspirating/dispensing plate 400 in accordance with a fourth embodiment.

Figure 6A:
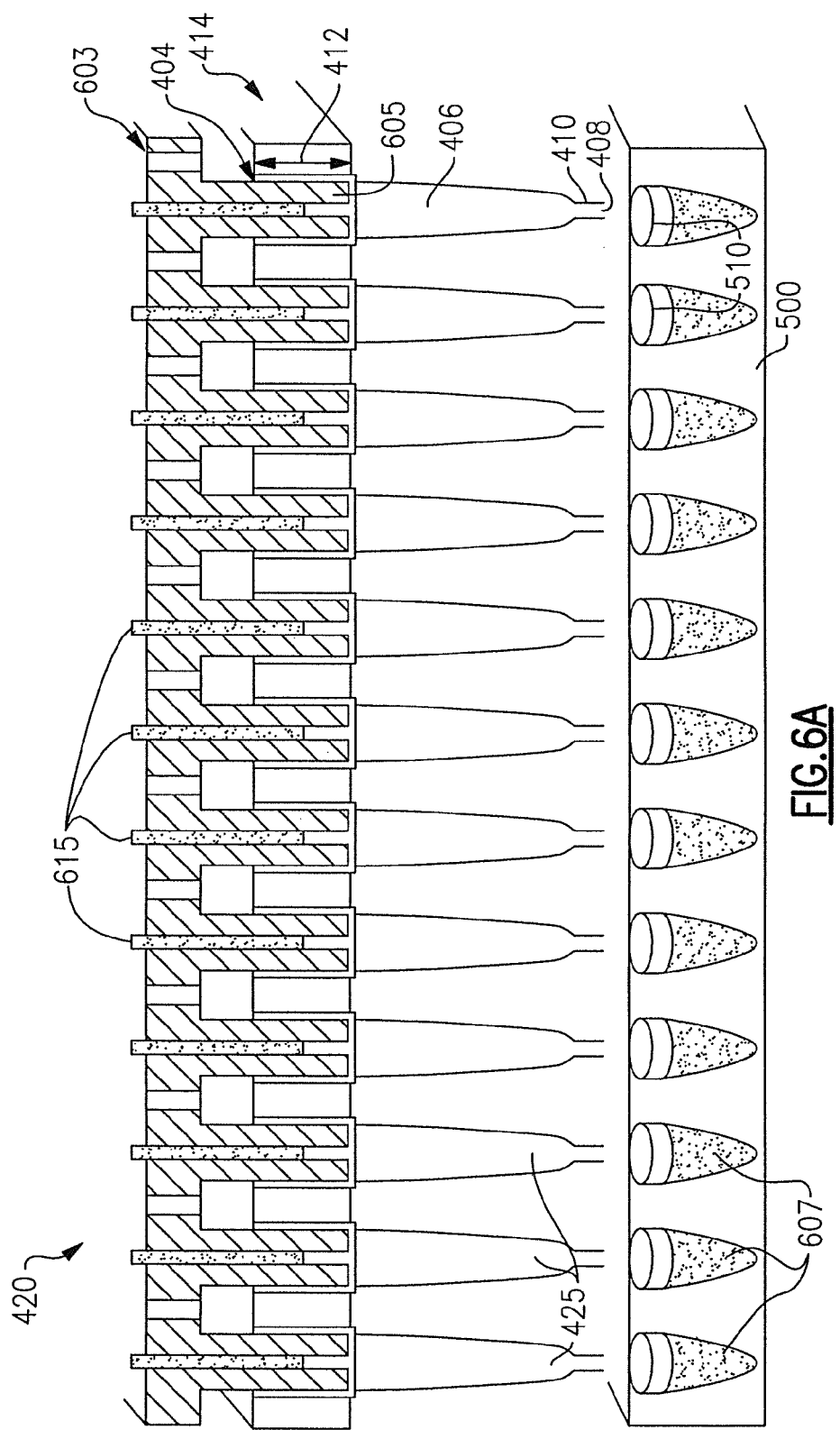

Referring to FIG. 6A, a cross section view of the row 420 of the fluid aspirating/dispensing members 425 of FIG. 4B is portrayed with the sealable input ports 408 aligned with the wells 510 of a microtiter plate 500. Appropriate robotic commands direct the metering mechanism 603 to align the proboscises 605 with the input ports 404 of the fluid aspirating/dispensing plate 400. After proper alignment, the metering system hermetically inserts the proboscises 605 through the open input ports 404 into the proboscis receptacle regions 412 of the fluid aspirating/dispensing members 425.

Figure 6C:
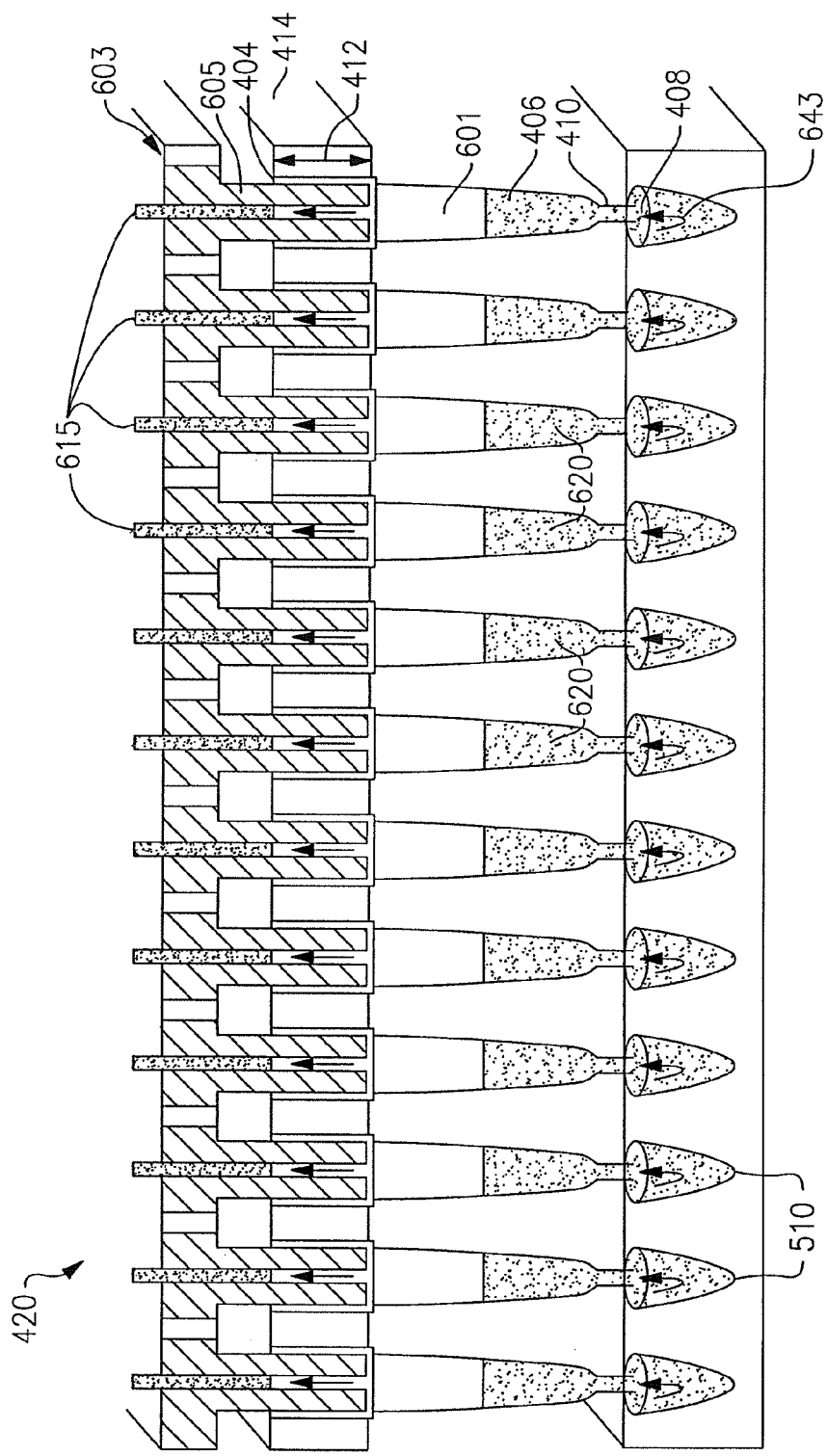

Referring to FIGS. 6B and 6C, the metering mechanism then aligns the sealable input ports 408 of the fluid aspirating/dispensing members 425 with the wells 510 of the microtiter plate 500 and immerses the sealable input ports 408 into the samples 607 within each well 510. The proboscises 605 of the metering mechanism 603 create a controlled amount of negative pressure within the internal volume of each of the fluid aspirating/dispensing members 425. The subsequent displacement of air 601 through the input ports 404 promotes the movement 643 of a defined volume of samples 607 into the sample cavities 406 of each of the fluid aspirating/dispensing members 425. The volume of the aspirated sample within each fluid aspirating/dispensing member 425 depends on the available volume within the sample cavities 406. In one example, an aliquot of between 0.1 to 1000 microliters of sample 607 is aspirated. In another example, an aliquot of between 0.1 to 300 microliters of sample 607 is aspirated. In yet another example, from 0.1 to 50 microliters of sample 607 is aspirated into the sample cavity 406 of each of the fluid aspirating/dispensing members 425.

Figure 6D:
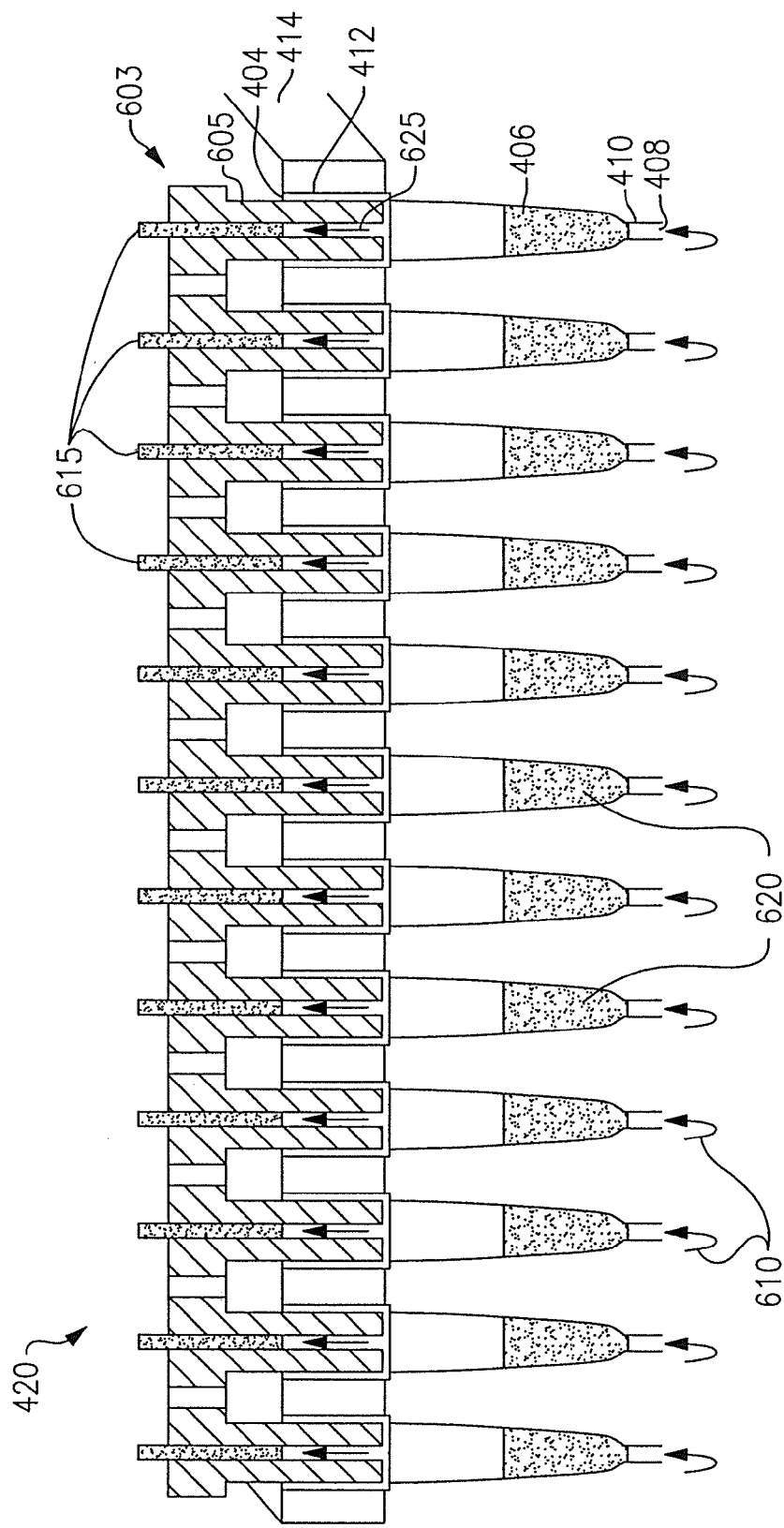

Referring now to FIG. 6D, the sealable input ports 408 are removed from the samples 607 in the wells 510. Again the proboscises 605 of the metering mechanism 603 exert a controlled amount of negative pressure within the internal volume of each of the fluid aspirating/dispensing members 425. The subsequent displacement of air within the internal cavities of the row 420 of fluid aspirating/dispensing members in the direction 625 causes the movement of the aspirated sample 620 into the sample cavity 406 proper and the aspiration of a measured amount of air 610 through the sealable input ports 408 into the sealable cavity 410 prior to heat sealing of the sealable input ports 408. This procedure averts the heating of the aspirated sample 620 and ensures a reliable seal.

Figure 6E:
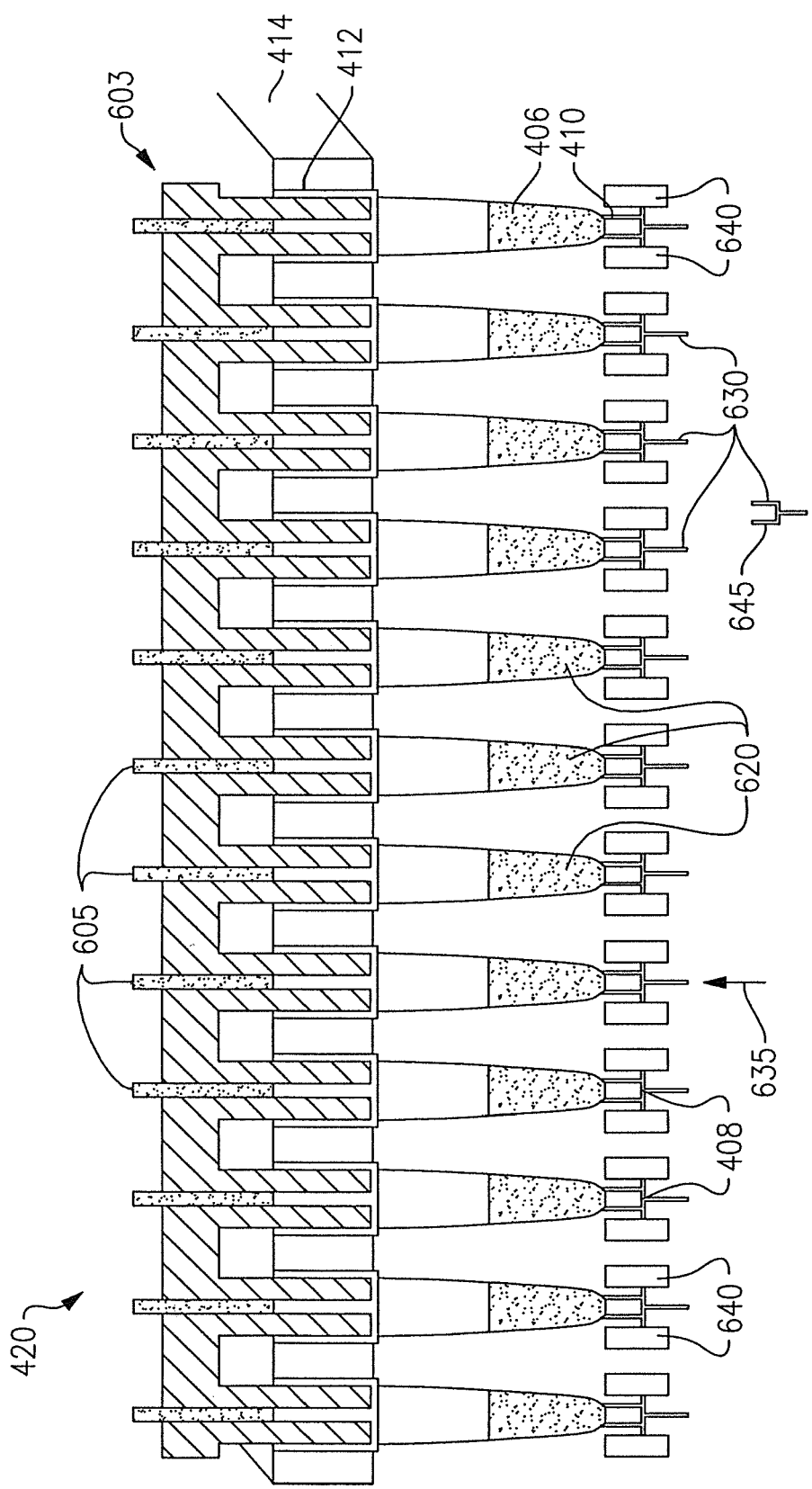
Figure 6F:
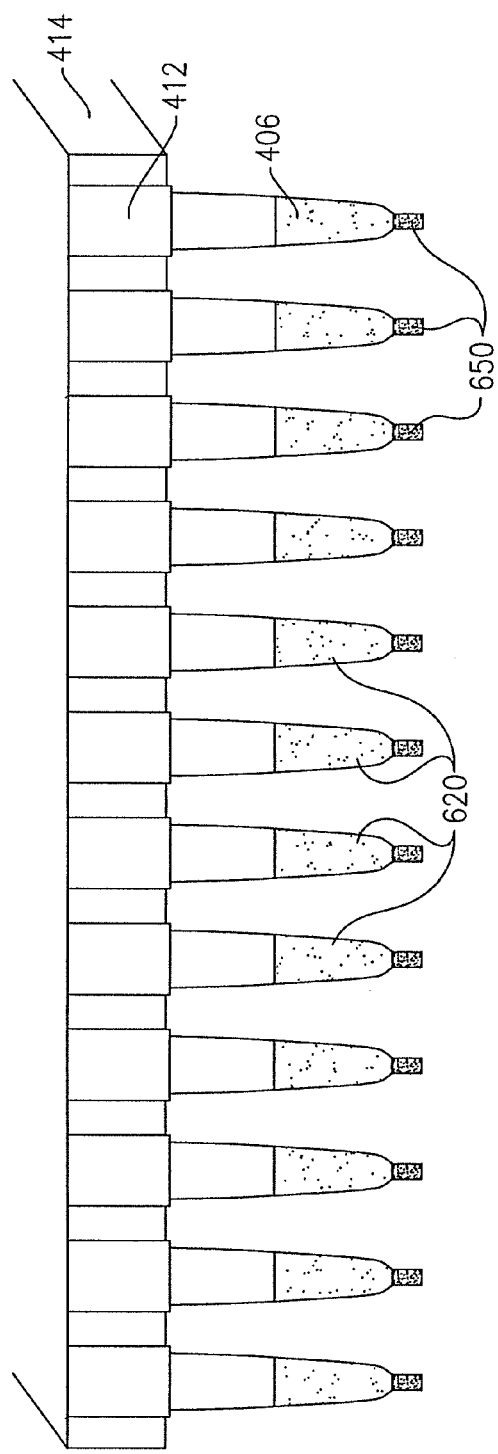

As shown in FIG. 6E, the walls of the sealable cavities 410 are then heated to the appropriate melting temperature using the row of heat sealing devices 640. After the walls of the heat sealable cavities 410 are heated, they are pressed in the direction 635 by the presses 630 to force the walls together and seal the open ends of the sealable input ports 408. In one version, the ends of the presses 630 are shaped in the form of a cup 645 that fits over the sealable input ports 408, thereby facilitating the fusion and molding of the input ports 408 into the sealed ends 650, depicted in FIG. 6F. In one version, metallic presses 630 are heated to the appropriate melting temperature and applied directly to the sealable input ports 408 for the melting and fusion of the walls of the sealable cavities 410. After sealing, the sealable input ports 408 are rapidly cooled to promote the solidification of the fused thermoplastic material thus producing a hermetically sealed fluid container or cuvette. The presses 630 and the proboscises 605 are then removed.

Figure 6G:
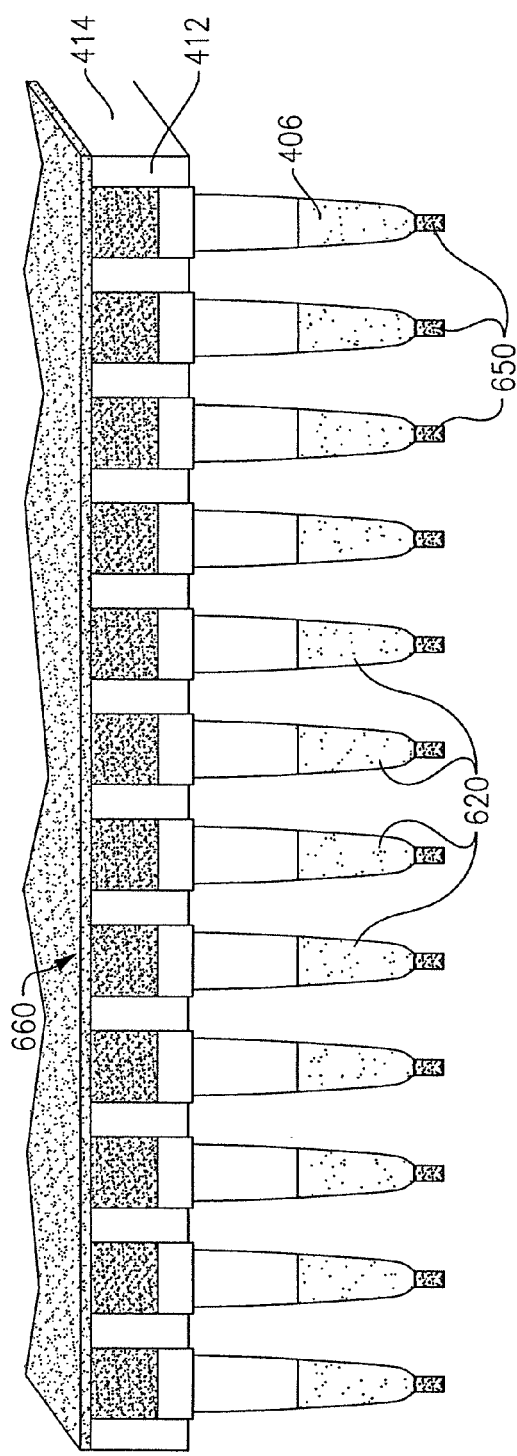

Referring to FIGS. 6G-I, an optional lid 660 is placed onto the fluid aspirating/dispensing plate 400 and hermetically seals the input ports 404 of the fluid aspirating/dispensing members. Lid 660 prevents the aspirated sample 620 from escaping the sample cavity 406 of each fluid aspirating/dispensing member and prevents cross-contamination of the aspirated samples 620. The fluid aspirating/dispensing plate 400 is then robotically placed into a fixed angle or swinging bucket rotor of a centrifuge and spun around a vertical axis 365 in the direction 370 for the time required to separate the particles within the aspirated sample from the rest of the sample. At the conclusion of the centrifugation, the particles within the aspirated samples 620 form pellets 670 at the bottom of the sample cavities 406. The lid 660 is then removed and the supernatants 680 can be collected and presented to the wet/dry components of the clinical analyzer.

In an alternative version, the sample cavities 406 may be preloaded with a separation barrier material, as defined herein, to facilitate the separation of the particulate phase from the liquid phase of the aspirated samples 620 during centrifugation. In another version, the sample cavities 406 may be pre-loaded with reagents, for example, reagents for agglutination or blood typing or antibodies attached to various particles as defined herein for immunoassays. In yet another version, the aspirated samples 620 within the fluid aspirating/dispensing members of a plate contain magnetic particles that can be separated from the rest of the aspirated samples 620 by placing the plate on a strong magnet according to protocols that are well known in the art.

As noted above, the herein described processing of samples in a plate of fluid aspirating/dispensing members is particularly amenable to automation for the rapid processing of STAT samples in urgent care facilities. Sample processing can be controlled by appropriate software programs running on a dedicated computer component of a clinical analyzer. In one version, the solid support 414 of a plate of fluid aspirating/dispensing members further comprises appendages to facilitate robotic handling and appropriate adapters for centrifugation.

The disclosure herein also provides for a kit format which comprises a package unit having one or more fluid aspirating/dispensing members of the subject disclosure and in some embodiments includes containers of various reagents. The kit may also contain one or more of the following items: buffers, instructions, and positive or negative controls. Kits may include containers of reagents mixed together in suitable proportions for performing the methods described herein. Reagent containers preferably contain reagents in unit quantities that obviate measuring steps when performing the subject methods. Kits may further comprise fluid aspirating/dispensing members pre-loaded with reagents.

PARTS LIST FOR FIGS. 1-6I

| | |
|---|---|
| 100 | fluid aspirating/dispensing member |
| 104 | input port |
| 106 | sample cavity |
| 108 | sealable input port |
| 110 | heat sealable cavity |
| 112 | proboscis receptacle region |
| 114 | cap |
| 116 | connector |
| 118 | vertical axis |
| 210 | movement of cap |
| 220 | open input port |
| 225 | closed input port |
| 310 | direction of movement of air |
| 320 | proboscis |
| 330 | sample |
| 335 | direction of movement of sample |
| 343 | aspiration of sample |
| 345 | aspirated sample |
| 347 | air space |
| 350 | metering mechanism |
| 353 | heat sealing device |
| 355 | sealed end |
| 357 | press |
| 360 | fluid aspirating/dispensing member in a centrifuge |
| 362 | direction of movement of press |
| 364 | cup |
| 365 | axis of rotation |

-continued
PARTS LIST FOR FIGS. 1-6I

| | |
|---|---|
| 367 | closed cap |
| 370 | direction of rotation |
| 375 | pellet |
| 380 | supernatant |
| 390 | probe |
| 400 | Fluid aspirating/dispensing plate with array of fluid aspirating/dispensing members |
| 404 | input ports |
| 406 | sample cavities |
| 408 | sealable input ports |
| 410 | sealable cavities |
| 412 | proboscis receptacle regions |
| 414 | solid support |
| 420 | row of fluid aspirating/dispensing members |
| 425 | fluid aspirating/dispensing member |
| 500 | microtiter plate |
| 510 | wells |
| 601 | direction of movement of air |
| 603 | array of metering mechanisms |
| 605 | array of proboscises |
| 607 | samples |
| 610 | aspiration of air |
| 615 | array of probes |
| 620 | aspirated samples |
| 625 | direction of movement of air |
| 630 | presses |
| 640 | heat sealer devices |
| 643 | aspiration of samples |
| 645 | cup |
| 650 | sealed ends |
| 660 | cover |
| 670 | pellets |
| 680 | supernatants |

While this invention has been particularly shown and described with references to preferred embodiments thereof, it will be understood by those skilled in the art that various changes in form and details may be made therein without departing from the intended scope of the invention encompassed by the following appended claims.

The invention claimed is:

1. A method of configuring a metering tip for use as a microcentrifuge tube in a clinical analyzer, said method comprising the steps of:
 a) providing a metering tip, said metering tip comprising an upper port, an opposing lower port and a sample cavity in fluid communication with each of said upper and lower ports;
 b) attaching said metering tip to a proboscis of said analyzer, said proboscis being heremetically sealed to the upper port;
 c) aspirating a fluid sample from a sample supply in said analyzer into said sample cavity through said lower port of said metering tip;
 d) aspirating a volume of air with said aspirated sample, said volume of air being aspirated into said tip through said lower port following the fluid sample aspiration step and providing an insulating layer between said sample and the lower port;
 e) sealing said lower port of said metering tip in order to create a fluid container;
 f) removing said proboscis and closing said upper port using a cap sized to releasably engage and cover said upper port; and
 g) separating particles in said fluid sample from the remainder of said fluid sample, wherein the separated particles and sample are retained within said sample cavity of said metering tip for detection of particles.

2. The method of claim 1, wherein the separating step is performed by centrifugation.

3. The method of claim 1, wherein the sealing step is performed using by heat-sealing the lower port of said metering tip.

4. The method of claim 1, wherein said cap is tethered to the upper port.

5. A method of separating particles in a plurality of fluid samples, said method comprising the steps of:
   a) loading a plurality of fluid aspirating/dispensing members into a supporting plate having a plurality of openings, said openings being sized for receiving a corresponding number of fluid aspirating/dispensing members, each of said fluid aspirating/dispensing members comprising an upper port, an opposing lower port and a sample cavity in fluid communication with each of said upper and lower ports;
   b) aspirating a plurality of samples into said sample cavities through said lower ports of each of said fluid aspirating/dispensing members;
   c) sealing the lower ports of each of said fluid aspirating/dispensing members to create a plurality of fluid containers; and
   d) separating particles in said sample from the remainder of the sample in each of said containers,
   wherein the separated particles and sample are retained within said sample cavity of each of said fluid aspirating/dispensing members for detection of the particles or sample.

6. The method of claim 5, wherein said supporting plate includes a linear array of openings for simultaneously retaining a linear array of fluid aspirating/dispensing members.

7. The method of claim 5, wherein said supporting plate includes a two-dimensional array of openings for simultaneously retaining a two-dimensional array of fluid aspirating/dispensing members.

8. The method of claim 5, wherein said loading step requires the attachment of said fluid aspirating/dispensing plate to a plurality of proboscises, said proboscises being part of a metering mechanism of said testing apparatus.

9. The method of claim 5, wherein said fluid aspirating/dispensing members are metering tips.

10. The method of claim 5, wherein said testing apparatus is a clinical analyzer.

11. The method of claim 5, wherein the separating step is performed by centrifugation.

12. The method of claim 5, further comprising a step, following said aspirating step, wherein the upper ports of each of said fluid aspirating/dispensing members are closed by a lid.

13. The method of claim 5, wherein the sealing step is performed by heat sealing said second ports of each of said members.

14. The method of claim 5, wherein said aspirating step includes the additional step of aspirating a volume of air between said sample cavity and said lower port of each of said fluid aspirating/dispensing members prior to sealing said lower port.

* * * * *